United States Patent [19]

Uchida et al.

[11] Patent Number: 5,215,999
[45] Date of Patent: Jun. 1, 1993

[54] QUINOLINE DERIVATIVE AND ANTIULCER AGENT CONTAINING SAID QUINOLINE DERIVATIVE

[75] Inventors: Minoru Uchida, Komatsushima; Seiji Morita; Kenji Otsubo, both Tokushima; Takefumi Shimizu; Katsuya Yamasaki, both of Tokushima, all of Japan

[73] Assignee: Otsuka Pharmaceutical Co., Ltd., Tokyo, Japan

[21] Appl. No.: 777,336

[22] PCT Filed: Mar. 27, 1991

[86] PCT No.: PCT/JP91/00404

§ 371 Date: Nov. 27, 1991

§ 102(e) Date: Nov. 27, 1991

[87] PCT Pub. No.: WO91/14677

PCT Pub. Date: Mar. 10, 1991

[30] Foreign Application Priority Data

Mar. 28, 1990 [JP] Japan .................... 3-81773

[51] Int. Cl.⁵ .................... A61K 31/47; C07D 215/44
[52] U.S. Cl. .................... 514/313; 546/160; 546/161
[58] Field of Search .................... 546/160, 161; 514/313

[56] References Cited

U.S. PATENT DOCUMENTS

| | | | |
|---|---|---|---|
| 4,284,768 | 8/1991 | Santilli | 544/128 |
| 4,342,804 | 8/1982 | Munson, Jr. et al. | 546/161 |
| 4,578,381 | 3/1986 | Uchida | 514/233 |
| 4,738,970 | 4/1988 | Uchida | 514/312 |
| 5,089,504 | 2/1992 | Ife et al. | 546/161 |

FOREIGN PATENT DOCUMENTS 0239129 9/1987 European Pat. Off.
0259174 3/1988 European Pat. Off.
8801621 3/1988 European Pat. Off.
0330485 8/1989 European Pat. Off.
0339768 11/1989 European Pat. Off.
55-147222 11/1980 Japan.

OTHER PUBLICATIONS

J. Med. Chem. 1990, 33, 527-533.
EP 0336 544 (abstract).
JP Laid-open 55-147222 (abstract).
JP Laid-open 63-22074.
JP Laid-open 63-22589 (abstract).
JP Laid-open 63-233960 (abstract).
JP Laid-open 64-40482
JP Laid-open 2-117663.
JP Laid-open 3-17078.

*Primary Examiner*—C. Warren Ivy
*Assistant Examiner*—James H. Turnipseed
*Attorney, Agent, or Firm*—Sughrue, Mion, Zinn, Macpeak & Seas

[57] ABSTRACT

The present invention discloses a quinoline derivative and salt thereof of the following general formula:

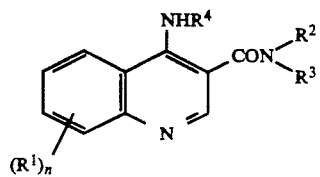

(wherein $R^1$, $R^2$, $R^3$, $R^4$ and n have the same meanings as defined above). Such a derivative is useful as an antiulcer agent.

17 Claims, No Drawings

QUINOLINE DERIVATIVE AND ANTIULCER AGENT CONTAINING SAID QUINOLINE DERIVATIVE

FIELD OF THE INVENTION

The present invention relates to a novel quinoline derivative, salt thereof and an antiulcer agent containing said quinoline derivative, and a method of producing said quinoline derivative.

DESCRIPTION OF THE PRIOR ART

As an antiulcer agent, there have been conventionally known quinoline derivatives disclosed by, for example, Japanese Unexamined Patent Applications Nos. 147222/1980 (and J. Med. Chem. 1990, 33, 527–533) and 40482/1989, European Laid-Open Patent Applications Nos. 0259174, 0330485 (and Austrian Laid-Open Patent Application No. 8930117), 0336544 and 0239129, and U.S. Patent Publications Nos. 4578381 and 473890. As so-called intermediate documents, there have been also known Japanese Unexamined Patent Applications Nos. 117663/1990 (laid-opened to the public on May, 2, 1990) and 17078/1991 (laid-opened to the public on Jan. 25, 1991).

As quinoline derivatives themselves, there have been known those set forth in Japanese Unexamined Patent Applications Nos. 22074/1988, 233960/1988 and 22589/1988, besides the documents above-mentioned.

It is an object of the present invention to provide a compound which is different in structure from any of the compounds above-mentioned, and which is useful as an antiulcer agent because it is superior in antiulcer function to any of the compounds above-mentioned.

DISCLOSURE OF THE INVENTION

The quinoline derivative in accordance with the present invention is a compound of the following general formula (1):

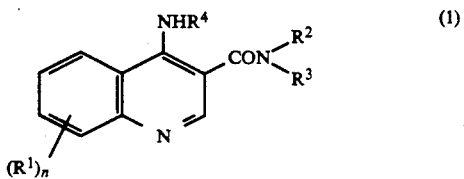

wherein $R^1$ is a lower alkoxy group, a halogen atom, a lower alkyl group, a lower alkylthio group, a lower alkanoyloxy-lower alkyl group, a halogen-substituted lower alkyl group or a hydroxy-group-substituted lower alkyl group; $R^2$ and $R^3$ may be same as or different from each other, and each is a hydrogen atom, a lower alkyl group, a halogen-substituted lower alkyl group, a cycloalkyl group having 3 to 8 carbon atoms, a cycloalkyl-lower alkyl group, a lower alkenyloxy group, a lower alkenyl group, a lower alkoxy-lower alkyl group, a phenyl lower alkyl group, a lower alkynyl group, a phenyl group having a lower alkyl group as a substituent group, or a hydroxy-group-substituted lower alkyl group; $R^4$ is a phenyl, tetrahydronaphthyl or naphthyl group which may have, as a substituent group on the phenyl ring, one or two groups selected from the group consisting of a lower alkyl group, a halogen atom, a lower alkoxy group, a lower alkylthio group, a lower alkanoyl group, a phenyl group, a cyano group, a lower alkyl sulfinyl group, a lower alkoxycarbonyl group, a lower alkenylthio group, a phenyl lower alkylthio group, a benzoyl group, a hydroxy-group-substituted lower alkyl group, a lower alkanoyloxy-lower alkyl group, a lower alkanoyloxy group and a hydroxyl group; n is 0, 1 or 2.

The compound of the present invention is adapted to decrease gastric acid secretion stimulated by a gastric acid secretion accelerating substance such as histamine, tetragastrin or foods, causing the compound to be useful for prevention and cure of a digestive ulcer of a human being and a mammal. The compound of the present invention is characterized in that its acid secretion inhibitory action is superior to and effective for a longer period of time as compared with a conventional antiulcer agent. Further, the compound in accordance with the present invention is remarkably effective in prevention and cure of an ulcer such as an aspirin ulcer or the like caused by an antiphlogistic pain-killer.

The production of a hydrochloric acid in the gastric mucous membrane is adjusted by a variety of pharmacological factors, but the biochemical mechanism in the $[H^+]$ ion production finally enters the rate-determining step. Recently, it has been found that ATPase adapted to be activated by $H^+$ and $K^+$ at the gastric wall cells controls the acid secretion. This enzyme is present specifically in the gastric wall cells and serves as a key enzyme of a proton pump. An inhibitor of this enzyme may serve as a useful acid secretion inhibitory agent. The compound of the present invention also produces an inhibitory effect on this enzyme. In particular, the present compound has both a gastric antisecretory activity and cytoprotective activity, thus controlling ulcer factors in both aggressive and defensive factors.

Further, the compound of the present invention is characterized in its greatly reduced toxicity and side effect.

Thus, the compound of the present invention is a novel one disclosed by none of the documents mentioned earlier.

The following will discuss examples of the respective groups defined by $R^1$, $R^2$, $R^3$ and $R^4$ in the general formula (1).

Examples of the lower alkoxy group include straight- or branched-chain alkoxy groups having 1 to 6 carbon atoms such as methoxy, ethoxy, propoxy, isopropoxy, butoxy, tert-butoxy, pentyloxy, hexyloxy groups and the like.

Examples of the halogen atom include fluorine, chlorine, bromine and iodine atoms, and the like.

Examples of the lower alkyl group include straight- or branched-chain alkyl groups having 1 to 6 carbon atoms such as methyl, ethyl, propyl, isopropyl, butyl, isobutyl, tert-butyl, pentyl, hexyl groups and the like.

Examples of the lower alkylthio group include straight- or branched-chain alkylthio groups having 1 to 6 carbon atoms such as methylthio, ethylthio, propylthio, isopropylthio, butylthio, tert-butylthio, pentylthio, hexylthio groups and the like.

Examples of the lower alkanoyloxy-lower alkyl group include straight- or branched-chain alkyl groups having 1 to 6 carbon atoms having straight- or branched-chain alkanoyloxy groups having 1 to 6 carbon atoms such as formyloxymethyl, acetyloxymethyl, propionyloxymethyl, butyryloxymethyl, pentanoyloxymethyl, hexanoyloxymethyl, 2-propionyloxyethyl, 1-butyryloxyethyl, 3-acetyloxypropyl, 4-isobutyryloxybutyl, 5-pentanoyloxypentyl, 6-tert-butylcarbonyloxyhexyl, 1,1-dimethyl-2-hexanoyloxyethyl, 2-methyl-3-acetyloxypropyl groups and the like.

Examples of the halogen-substituted lower alkyl group include straight- or branched-chain alkyl groups having 1 to 6 carbon atoms in which 1 to 3 halogen atoms are substituted, such as chloromethyl, bromomethyl, iodomethyl, fluoromethyl, dichloromethyl, dibromomethyl, difluoromethyl, trichloromethyl, tribromomethyl, trifluoromethyl, 2-chloroethyl, 2-bromoethyl, 2-fluoroethyl, 1,2-dichloroethyl, 2,2-difluoroethyl, 1-chloro-2-fluoroethyl, 2,2,2-trifluoroethyl, 2,2,2-trichloroethyl, 3-fluoropropyl, 3,3,3-trichloropropyl, 4-chlorobutyl, 5-chloroheptyl, 6-chlorohexyl, 3-chloro-2-methylpropyl groups and the like.

Examples of the hydroxy-group-substituted lower alkyl group include straight- or branched-chain alkyl groups having 1 to 6 carbon atoms and having, as a substituent group, a hydroxyl group such as hydroxymethyl, 2-hydroxyethyl, 1-hydroxyethyl, 3-hydroxypropyl, 4-hydroxybutyl, 1,1-dimethyl-2-hydroxyethyl, 5-hydroxypentyl, 6-hydroxyhexyl, 2-methyl-3-hydroxypropyl groups and the like.

Examples of the cycloalkyl group having 3 to 8 carbon atoms include cyclopropyl, cyclobutyl, cyclopentyl, cyclohexyl, cycloheptyl, cyclooctyl groups and the like.

Examples of the cycloalkyl lower-alkyl group include alkyl groups substituted by cycloalkyl group having 3 to 8 carbon atoms, in each of which the alkyl moiety has a straight- or branched-chain alkyl group having 1 to 6 carbon atoms, such as cyclopropylmethyl, 2-cyclobutylethyl, 1-cyclopentylethyl, 3-cyclohexylpropyl, 4-cycloheptylbutyl, 6-cyclooctylhexyl, 5-cyclopropylpentyl, 1,1-dimethyl-2-cyclopropylethyl, 2-methyl-3-cyclohexylpropyl, cyclohexylmethyl groups and the like.

Examples of the lower alkenyloxy group include straight- or branched-chain alkenyloxy groups having 2 to 6 carbon atoms such as vinyloxy, allyloxy, 2-butenyloxy, 3-butenyloxy, 1-methylallyloxy, 2-pentenyloxy, 2-hexenyloxy groups and the like.

Examples of the lower alkenyl group include straight- or branched-chain alkenyl groups having 2 to 6 carbon atoms such as vinyl, allyl, 2-butenyl, 3-butenyl, 1-methylallyl, 2-pentenyl, 2-hexenyl groups and the like.

Examples of the lower alkoxy-lower alkyl group include straight- or branched-chain alkyl groups having 1 to 6 carbon atoms in each of which 1 to 6 straight- or branched-chain alkoxy groups are substituted, such as methoxyethyl, ethoxymethyl, 2-ethoxyethyl, 2-methoxyethyl, 3-methoxypropyl, 4-ethoxybutyl, 6-propoxyhexyl, 5-isopropoxypentyl, 1,1-dimethyl-2-butoxyethyl, 2-methyl-3-tert-butoxypropyl, 2-penthyloxyethyl, hexyloxymethyl groups and the like.

Examples of the lower alkynyl group include straight- or branched-chain alkynyl groups having 2 to 6 carbon atoms such as ethynyl, 2-propynyl, 2-butynyl, 3-butynyl, 1-methyl-2-propynyl, 2-pentynyl, 2-hexynyl groups and the like.

Examples of the phenyl lower alkyl group include phenyl alkyl groups in each of which alkyl moiety is a straight- or branched-chain alkyl group having 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl groups and the like.

Examples of the lower alkanoyl group include straight- or branched-chain alkanoyl groups having 1 to 6 carbon atoms such as formyl, acetyl, propionyl, butyryl, isobutyryl, pentanoyl, tert-butylcarbonyl, hexanoyl groups and the like.

Examples of the lower alkylsulfinyl group include straight- or branched-chain alkylsulfinyl groups having 1 to 6 carbon atoms such as methylsulfinyl, ethylsulfinyl, isopropylsulfinyl, butylsulfinyl, tert-butylsulfinyl, pentylsulfinyl, hexylsulfinyl groups and the like.

Examples of the lower alkoxycarbonyl group include alkoxycarbonyl groups in each of which alkoxy moiety is a straight- or branched-chain alkoxy group having 1 to 6 carbon atoms, such as methoxycarbonyl, ethoxycarbonyl, propoxycarbonyl, isopropoxycarbonyl, butoxycarbonyl, tert-butoxycarbonyl, penthyloxycarbonyl, hexyloxycarbonyl groups and the like.

Examples of the lower alkenylthio group include straight- or branched-chain alkenylthio groups having 2 to 6 carbon atoms such as vinylthio, allylthio, 2-butenylthio, 3-butenylthio, 1-methylallylthio, 2-pentenylthio, 2-hexenylthio groups and the like.

Examples of the phenyl lower alkylthio group include phenylalkylthio groups in each of which alkyl moiety is a straight- or branched-chain alkyl group having 1 to 6 carbon atoms, such as benzylthio, 2-phenylethylthio, 1-phenylethylthio, 3-phenylpropylthio, 4-phenylbutylthio, 1,1-dimethyl-2-phenylhexylthio, 5-phenylpenthylthio, 6-phenylhexylthio, 2-methyl-3-phenylpropylthio groups and the like.

Examples of the lower alkanoyloxy group include straight- or branched-chain alkanoyloxy groups having 1 to 6 carbon atoms such as formyloxy, acetyloxy, propionyloxy, butyryloxy, isobutyryloxy, pentanoyloxy, tert-butylcarbonyloxy, hexanoyloxy groups and the like.

Examples of the phenyl group having a lower alkyl group as a substituent group include phenyl groups each of which has one straight- or branched-chain alkyl group having 1 to 6 carbon atoms, such as 2-methylphenyl, 3-methylphenyl, 4-methylphenyl, 2-ethylphenyl, 3-ethylphenyl, 4-ethylphenyl, 2-propylphenyl, 3-isopropylphenyl, 2-butylphenyl, 3-tert-butylphenyl, 2-penthylphenyl, 3-hexylphenyl groups and the like.

When n is 2 in the present invention, two substituent groups $R^1$ may be same as or different from each other.

The compound of the present invention containing an optical isomer is also included in the present invention.

The compound of the present invention may be produced by any of a variety of methods, of which preferable one is shown, for example, in the following reaction formula.

Reaction Formula

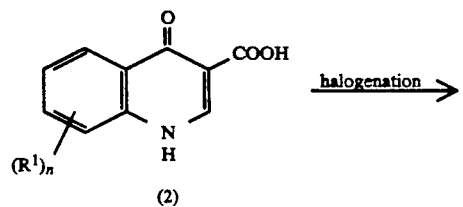

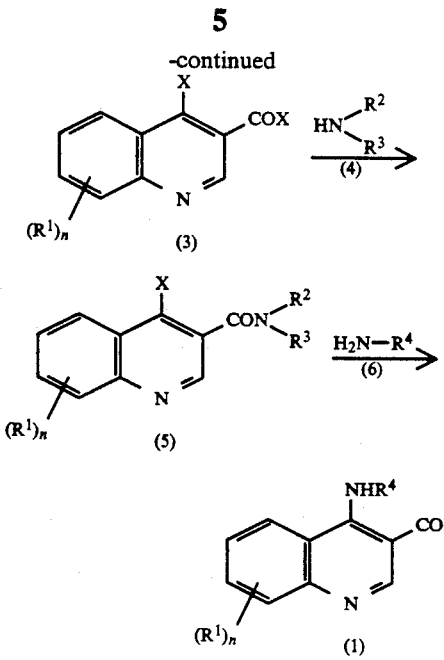

wherein $R^1$, $R^2$, $R^3$, $R^4$ and n have the same meanings as defined above, and X is a halogen atom.

The halogenation of the compound of the general formula (2) is carried out by reacting the compound (2) with a halogenation agent under the absence or presence of a suitable inert solvent. As the inert solvent, there may be used any of known inert solvents as far as it exerts no influence upon the reaction. Examples of the inert solvent include aromatic hydrocarbons such as benzene, toluene, xylene and the like, halogenated hydrocarbons such as dichloromethane, chloroform, carbon tetrachloride and the like, ethers such as dioxane, tetrahydrofuran, diethylether and the like, dimethylformamide (DMF), dimethylsulfoxide (DMSO) and the like. As the halogenation agent, there may be used, without any restrictions, any of known halogenation agents which can convert the hydroxy group in the carboxy group into halogen. Examples of the halogenation agent include thionylchloride, phosphorus oxychloride, phosphorus oxybromide, phosphorus pentachloride, phosphorus pentabromide and the like. The proportion of the halogenation agent to the compound (2) is not limited to a certain value but may vary over a wide range. However, when the reaction is carried out in the absence of a solvent, the halogenation agent is generally used in an excessive amount with respect to the amount of the compound (2). When the reaction is carried out in the presence of a solvent, the proportion of the halogenation agent to the compound (2) is generally at least about twice molar amount and preferably in a range from 2- to 10-time molar amount. No particular restrictions are imposed on the reaction temperature and time. However, the reaction is generally conducted at a temperature from about room temperature to about 100° C. for about 30 minutes to about 6 hours.

The reaction between the compound of the general formula (3) and the compound of the general formula (4) is generally carried out according to a Schötten-Baumann reaction. For example, the reaction is carried out in a suitable inert solvent under the presence of a basic compound. As the basic compound, there may be used, without any restrictions, any of known basic compounds used in a Schötten-Baumann reaction. Examples of the basic compound include tertiary organic bases such as triethyl amine, trimethyl amine, pyridine, dimethylaniline, N-methylmorpholine, 1,5-diazabicyclo [4.3.0] nonene-5 (DBN), 1,8-diazabicyclo [5.4.0] undecen-7 (DBU), 1,4-diazabicyclo [2.2.2] octane (DABCO) and the like, and inorganic basic compounds such as carbonates including potassium carbonate, sodium carbonate, potassium bicarbonate, sodium bicarbonate and the like. As the solvent, there may be used, without any restrictions, any of known inert solvents as far as it exerts no influence upon the reaction. Examples of the inert solvents include: halogenated hydrocarbons such as methylene chloride, chloroform, dichloroethane and the like; aromatic hydrocarbons such as benzene, toluene, xylene and the like; ethers such as diethylether, tetrahydrofuran, dioxane, dimethoxyethane and the like; esters such as methyl acetate, ethyl acetate and the like; non-protic polar solvents such as N,N-dimethylformamide, dimethylsulfoxide, hexamethylphosphoric triamide and the like; pyridine; acetone; acetonitrile; water; and a mixed solvent containing at least two of the solvent examples above-mentioned. The proportion of the compound (4) to the compound (3) is not limited to a specific value, but may vary over a wide range. However, such a proportion is generally at least about an equimolar amount and preferably in a range from an equimolar amount to 5-time molar amount. The reaction above-mentioned is carried out, generally for 5 minutes to 12 hours, at a temperature generally from about −20° to about 100° C. and preferably from 0° to 80° C.

The reaction between the compound (5) and the compound (6) is carried out under the absence or presence of a suitable inert solvent for about 1 to about 12 hours at a temperature from about room temperature to about 200° C. and preferably from 50° to 130° C. Examples of the inert solvent include: ethers such as dioxane, tetrahydrofuran, ethylene glycol dimethylether, diethylether and the like; aromatic hydrocarbons such as benzene, toluene, xylene and the like; lower alcohols such as methanol, ethanol, isopropanol and the like; polar solvents such as dimethylformamide, dimethylsulfoxide, hexamethylphosphoric triamide, acetone, acetonitrile, N-methylpyrrolidone and the like; and a mixed solvent containing at least two of the solvent examples above-mentioned. The reaction above-mentioned is carried out with the basic compound used as a deacidification agent. Examples of the basic compound include carbonates such as potassium carbonate, sodium carbonate, potassium bicarbonate, sodium bicarbonate and the like; and tertiary amines such as triethylamine, tripropylamine, pyridine, quinoline and the like. The compound (6) may also serve as a deacidification agent. The reaction above-mentioned may also be carried out with a reaction accelerator added as necessary. Examples of the reaction accelerator include iodide alkali metal compounds such as potassium iodide, sodium iodide and the like, and hexamethylphosphoric triamide. The proportion of the compound (6) to the compound (5) in the reaction above-mentioned is not specially limited to a certain value, but may vary over a wide range. However, such a proportion is generally at least about an equimolar amount and preferably in a range from an equimolar amount to a 3-time molar amount. When the compound (6) also serves as a deacidification agent, the compound (6) is generally used in an excessive amount with respect to the amount of the compound (5).

The compound (1) of the present invention can readily form salt together with a pharmaceutically acceptable acid of the general type. Examples of the acid include inorganic acids such as sulphuric acid, nitric acid, hydrochloric acid, hydrobromic acid and the like, and organic acids such as acetic acid, p-toluenesulfonic acid, methanesulfonic acid, ethanesulfonic acid, oxalic acid, maleic acid, citric acid, tartanic acid, succinic acid, benzoic acid and the like.

Out of examples of the compound (1) of the present invention, a compound containing an acidic group can form salt together with a pharmaceutically acceptable basic compound. Examples of the basic compound include metallic hydroxides such as sodium hydroxide, potassium hydroxide, lithium hydroxide, calcium hydroxide and the like, alkali metal carbonates or bicarbonates such as sodium carbonate, sodium bicarbonate and the like, and alkali metal alcoholates such as sodium methylate, potassium ethylate and the like.

The target compound to be prepared by the method shown by the reaction formula above-mentioned can be separated from the reaction system by general separating means, and further refined. As such separating and refining means, there may be used any of distillation, recrystallization, column chromatography, ion-exchange chromatography, preparative thin-layer chromatography, solvent extraction methods and the like.

The effective components thus prepared are useful as an antiulcer agent, and may be used in the form of a general pharmaceutical composition. The pharmaceutical composition may be prepared with the use of diluents or excipients such as a filler, an extender filler, a binder, a humidifying agent, a disintegrator, a surfactant, a lubricant and the like which may be generally used. According to the curing purpose, the pharmaceutical composition may be made in any of forms such as tablet, pill, powder medicine, liquid medicine, suspension, emulsion, granule, capsule, suppository, injectable preparation (liquid medicine, suspension and the like) and the like. Of these forms, the form of injectable preparation is preferable.

When making the pharmaceutical composition in the form of tablet, there may be widely used any of a variety of carriers conventionally used in this field. Examples of the carrier include: an excipient such as lactose, white sugar, sodium chloride, glucose, urea, starch, potassium carbonate, kaoline, crystal cellurose, silica and the like; a binder such as water, ethanol, propanol, simple syrup, a glucose liquid, a starch liquid, a gelatin solution, carboxymethylcellulose, shellac, methylcellulose, potassium phosphate, polyvinyl pyrrolidone and the like; a disintegrator such as dry starch, sodium alginate, agar powder, laminaria powder, sodium bicarbonate, potassium carbonate, polyoxyethylene sorbitan fatty esters, sodium lauryl sulfate, monoglyceride stearate, starch, lactose and the like; a disintegration restraining agent such as white sugar, stearin, cacao butter, hydrogenated oil and the like; an absorption accelerating agent such as quaternary ammonium base, sodium lauryl sulfate and the like; a humectant such as glycerin, starch and the like; an adsorbent such as starch, lactose, kaolin, bentonite, colloidal silicic acid and the like; a lubricant such as refined talc, salt stearate, boric acid powder, polyethylene glycol and the like. As necessary, tablets may be coated with a normal film to prepare sugar-coated tablets, gelatin-coated tablets, enteric-coated tablets, film-coated tablets or tablets comprising two or more layers. In molding the pharmaceutical composition in the form of pills, there may be used a variety of carriers known in the field. Examples of such carriers include an excipient such as glucose, lactose, starch, cacao grease, hydrogenated vegetable oil, kaolin, talk and the like, a binder such as powdered acacia gum, powdered traganth, gelatin, ethanol and the like, and a disintegrator such as laminaria, agar and the like. In molding the pharmaceutical composition in the form of suppository, there may be used any of a variety of known carriers. Examples of such carriers include esters such as polyethylene glycol, cacao grease, higher alcohol and the like, gelatin, semisynthetic glyceride and the like. The pharmaceutical composition may be made in the form of capsules by charging hard gelatin capsules, soft capsules and the like with a mixture of the compound of effective components with carriers selected from the carriers above-mentioned according to a conventional manner. When preparing the pharmaceutical composition in the form of injectable preparation, the resulting solution, emulsion and suspension are preferably sterilized and made isotonic with respect to the blood. In this connection, there may be used any of diluents generally used in the field. Examples of such diluents include water, ethyl alcohol, macrogall, propylene glycol, ethoxylated isostearil alcohol, polyoxylated isostearil alcohol, and polyoxyethylene sorbitan fatty esters. The pharmaceutical composition may contain salt, glucose or glycerin in an amount sufficient to prepare an isotonic solution. There may also be added a solubilizer, a buffer agent, a pain-alleviating agent and the like of the normal type. As necessary, the pharmaceutical composition may contain a coloring agent, a preserving agent, spicery, flavor, a sweetening agent or other pharmaceutical products.

The proportion of the compound of effective components to the pharmaceutical preparation is not limited to a certain value but may vary over a wide range. However, such a proportion is in a range from about 1 to about 70% by weight and preferably from about 5 to about 50% by weight.

The administration method of the pharmaceutical composition is not particularly limited and can be selected according to the form of the preparation, the patient's age and gender, other conditions and the symptom of a disease. For example, the tablets, pills, liquid preparations, suspensions, emulsions, granules and capsules are orally administered. The injectable preparations are intravenously administered either alone or together with ordinary auxiliary agents such as glucose, amino acids and the like. Further, the injectable preparations may be singly administered intramuscularly, intracutaneously, subcutaneously or intraperitoneally, as necessary. The suppository is administered intrarectally.

The dosage of the pharmaceutical composition is suitably selected according to the purpose of use, the patient's age and gender, the symptoms of a disease and the like. Usually, the compound of effective components is used in an amount from about 2 to about 24 mg per 1 kg of patient's weight, and the pharmaceutical composition may be administered 1 to 4 times per day.

Field of the Industrial Applicability

The compound of the present invention is useful for prevention and cure of a digestive ulcer of a human being and a mammal, and is characterized in that its acid secretion inhibitory action is superior to and effective for a longer period of time as compared with a conventional antiulcer agent. Further, the compound in accordance with the present invention is remarkably effective in prevention and cure of an ulcer such as an aspirin ulcer or the like caused by an antiphlogistic pain-killer.

Further, the compound of the present invention presents an inhibitory action on ATPase. In particular, the present compound has both a gastric antisecretory activity and a cytoprotective activity, thus controlling ulcer factors in both aggressive and defensive factors.

Further, the compound of the present invention is characterized in its greatly reduced toxicity and side effect.

EXAMPLES

The following will discuss in more detail the present invention with reference to Examples thereof and Reference Examples, which are merely shown by way of example.

Reference Example 1

Ten ml of thionyl chloride was added to 1.5 g of 8-methoxy-4(1H)-quinolone-3-carboxylic acid, and the reaction mixture was refluxed for one hour. The reaction solution was concentrated under reduced pressure to give 4-chloro-8-methoxy quinoline-3-carboxylic acid chloride.

0.47 G of allylamine and 0.94 g of potassium carbonate were dissolved in 50 ml of acetone and 20 ml of water. While the resultant reaction solution was stirred under ice-cooling, the acid chloride (crystal) thus prepared was added, as crushed as it was, to the reaction solution. After the resultant reaction mixture was stirred at the same temperature for one hour, acetone was distilled off. The residue was then poured into water and the precipitation was filtered off to give 1.5 g of N-(2-propenyl)-4-chloro-8-methoxyquinoline-3-carboxamide in the form of a brown prism as recrystallized from ethyl acetate and n-hexane. mp. 114° to 116° C.

In the same manner as in Reference Example 1, there were prepared the compounds shown in Table 1 with suitable starting materials used.

TABLE 1

(R$^1$)n— [quinoline structure with Cl at 4-position and CON(R$^2$)(R$^3$) at 3-position]

| Reference Example | R$^1$ | R$^2$ | R$^3$ | | NMR (CDCl$_3$)δppm |
|---|---|---|---|---|---|
| 2 | 8-OCH$_3$ | cyclohexyl— | H | n = 1 | 1.20–1.60(5H, m), 1.60–1.90 (3H, m), 2.00–2.20(2H, m), 4.10(3H, s), 4.00–4.20(1H, m) 6.20(1H, brs), 7.15(1H, d, J=7.8Hz), 7.60(1H, t, J=7.8Hz), 7.82(1H, d, J=8.6Hz), 8.97(1H, s) |
| 3 | H | C$_2$H$_5$ | H | n = 1 | 1.32(3H, t, J=7.3Hz), 3.59(2H, q, J=7.3Hz) 6.50(1H, brs), 7.68(1H, t, J=7.0Hz), 7.81(1H, t, J=7.0Hz), 8.11(1H, d, J=8.8Hz), 8.27(1H, d, J=8.3Hz) 8.99(1H, s) |
| 4 | 8-OCH$_3$ | —CH$_2$CH=CH$_2$ | —CH$_2$CH=CH$_2$ | n = 1 | 3.70–4.70(4H, m), 4.11(3H, s) 5.10–5.40(4H, m), 5.60–6.10 (2H, m), 7.17(1H, d, J=6.4Hz), 7.63(1H, t, J=6.4Hz), 7.85 (1H, d, J=6.8Hz), 8.76(1H, s) |
| 5 | 8-OCH$_3$ | —CH$_2$CH$_2$OCH$_3$ | H | n = 1 | 3.40(3H, s), 3.62(2H, t, J= 4.5Hz), 3.74(2H, q, J=5.3Hz), 4.10(3H, s), 6.74(1H, brs), 7.16(1H, d, J=7.3Hz), 7.61(1H, t, J=8.5Hz), 7.85(1H, dd, J=1.1Hz, 10Hz), 9.00(1H, s) |
| 6 | 8-OCH$_3$ | —CH(CH$_3$)(CH$_2$CH$_3$) | H | n = 1 | 1.04(3H, t, J=7.5Hz), 1.31 (3H, d, J=6.6Hz), 1.65(2H, q, J=7.5Hz), 4.10(3H, s), 4.10–4.30(1H, m), 6.22(1H, brs), 7.14(1H, d, J=7.8Hz), 7.58(1H, t, J=7.8Hz), 7.79(1H, dd, J=1.1Hz, 8.6Hz), 8.94(1H, s) |
| 7 | 8-OCH$_3$ | —CH$_2$C≡CH | H | n = 1 | 2.34(1H, t, J=2.6Hz), 4.10(3H, s), 4.35(2H, dd, J= 2.6Hz, 6Hz), 6.76(1H, brs), 7.16(1H, d, J=7Hz), 7.60(1H, t, J=8.6Hz), |

TABLE 1-continued

| Reference Example | R¹ | R² | R³ | | NMR (CDCl₃)δppm |
|---|---|---|---|---|---|
| | | | | | 7.80(1H, dd, J=1.1Hz, 8Hz), 8.98(1H, s) |
| 8 | 8-OCH₃ | —CH₂CH₂CH₂OH | H | n = 1 | 1.87(2H, q, J=5.5Hz), 2.68 (1H, brs), 3.70(2H, q, J=6.1 Hz), 3.82(2H, t, J=5.7Hz), 4.08(3H, s), 7.10(1H, brs), 7.15(1H, d, J=7.7Hz), 7.59 (1H, t, J=7.8Hz), 7.80(1H, dd, 8.95(1H, s) |
| 9 | 8-F | —CH₂CH=CH₂ | H | n = 1 | 4.10–4.30(2H, m), 5.20–5.50 (2H, m), 5.58–6.20(1H, m), 6.60(1H, brs), 7.40–7.80(2H, m), 8.00–8.20(1H, m), 8.99(1H, s) |
| 10 | 8-OCH₃ | ▷ | H | n = 1 | 0.30–1.00(4H, m), 2.90–3.10 (1H, m), 4.09(3H, s), 6.58(1H, brs), 7.13(1H, d, J=7.7Hz), 7.57(1H, t, J=7.9Hz), 7.77(1H, d, J=8.5Hz), 8.92(1H, s) |
| 11 | 8-CH₃ | —CH₂CH=CH₂ | H | n = 1 | 2.81(3H, s), 4.18(2H, t, J= 4.5Hz), 5.10–5.40(2H, m), 5.90–6.10(1H, m), 6.60(1H, brs), 7.50–7.70(2H, m), 8.25(1H, d, J=6.7Hz), 9.20(1H, s) |
| 12 | 8-OC₂H₅ | —CH₂CH=CH₂ | H | n = 1 | 1.60(3H, t, J=5.6Hz), 4.10–4.30(2H, m), 4.30(2H, q, J=5.6Hz), 5.20–5.40(2H, m), 5.90–6.10(1H, m), 6.88(1H, brs), 7.10(1H, d, J=6.2Hz), 7.52(1H, t, J=6.4Hz), 7.72(1H, d, J=6.9Hz), 8.92(1H, s) |
| 13 | 7-Cl, 8-OCH₃ | —CH₂CH=CH₂ | H | n = 2 | 4.15(3H, s), 4.10–4.30(2H, m) 5.20–5.50(2H, m), 5.80–6.10(1H, m), 7.64(1H, d, J=9.1Hz), 7.94(1H, d, J=9.1Hz), 9.01(1H, s) |
| 14 | 5-CH₃, 8-OCH₃ | —CH₂CH=CH₂ | H | n = 2 | 2.88(3H, s), 4.04(3H, s), 4.18(2H, t, J=5.6Hz), 5.30–5.50(2H, m), 5.90–6.10(1H, m), 6.54(1H, brs), 6.97(1H, d, J=8.1Hz), 7.29(1H, d, J=8.4Hz), 8.75(1H, s) |
| 15 | 8-SCH₃ | —CH₂CH=CH₂ | H | n = 1 | 2.57(3H, s), 4.10–4.20(2H, m) 5.20–5.40(2H, m), 5.90–6.10 (1H, m), 6.48(1H, brs), 7.45(1H, d, J=6.0Hz), 7.60(1H, t, J=6.0Hz), 7.96(1H, dd, J=1.1Hz, 6.7Hz), 8.98(1H, s) |
| 16 | 8-C₂H₅ | —CH₂CH=CH₂ | H | n = 1 | 1.36(3H, t, J=7.5Hz), 3.29 (2H, q, J=7.5Hz), 4.10–4.30 (2H, m), 5.20–5.40(2H, m), 5.90–6.10(1H, m), 6.43(1H, brs), 7.60–7.70(2H, m) 8.15(1H, dd, J=2.0Hz, 7.9Hz), 9.04(1H, s) |
| 17 | 8-CH₂OCOCH₃ | —CH₂CH=CH₂ | H | n = 1 | 2.16(3H, s), 4.16–4.22(2H, m) |

TABLE 1-continued

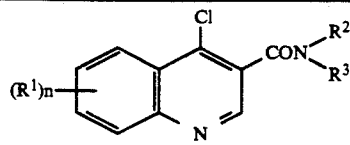

| Reference Example | R¹ | R² | R³ | | NMR (CDCl₃)δppm |
|---|---|---|---|---|---|
| | | | | | 5.22–5.40(2H, m), 5.82(2H, s) 5.90–6.06(1H, m), 6.40(1H, brs), 7.69(1H, t, J=7.2Hz), 7.87(1H, d, J=7.2Hz), 8.29(1H, dd, J=1.1Hz, 8.4Hz), 9.06(1H, s) |
| 18 | 8-CH—CH₃<br>      \|<br>    OCOCH₃ | —CH₂CH=CH₂ | H | n = 1 | 1.64(3H, d, J=6.6Hz), 2.14 (3H, s), 4.17(2H, t, J=5.7Hz), 5.21–5.39(2H, m), 5.88–6.08 (1H, m), 6.41(1H, brs), 7.04 (1H, q, J=6.6Hz), 7.68(1H, t, J=8.4Hz), 7.86(1H, d, J=6.8 Hz), 8.24(1H, dd, J=1.4Hz, 8.4Hz), 9.03(1H, s) |
| 19 | 8-CH(CH₃)₂ | —CH₂CH=CH₂ | H | n = 1 | 1.37(3H, d, J=6.9Hz), 4.17–4.22(2H, m), 4.22(2H, q, J=6.9Hz), 5.22–5.40(2H, m), 5.90–6.06(1H, m), 6.36(1H, brs), 7.62–7.74(2H, m), 8.17(1H, dd, J=1.9Hz, 7.9Hz), 9.07(1H, s) |
| 20 | 8-OCH₃ | —C₂H₅ | H | n = 1 | 1.33(3H, t, J=7.3Hz), 3.59 (2H, q, J=7.3Hz), 4.10(3H, s), 6.36(1H, brs), 7.15(1H, d, J=7.5Hz), 7.60(1H, t, J=7.9Hz), 7.82(1H, d, J=8.6Hz), 8.97(1H, s) |
| 21 | 8-C₂H₅ | —C₂H₅ | H | n = 1 | 1.31(3H, t, J=7.3Hz), 1.35 (3H, t, J=7.5Hz), 3.29(2H, q, J=7.5Hz), 3.58(2H, q, J=7.3 Hz), 6.34(1H, brs), 7.55–7.67(2H, m), 8.13(1H, dd, J=1.9Hz, 7.9Hz), 9.00(1H, s) |
| 22 | 8-OCH₃ | —CH₂CH₂CH₃ | H | n = 1 | 1.05(3H, t, J=7.5Hz), 1.66–1.77(2H, m), 3.51(2H, q, J=6Hz), 4.10(3H, s), 6.39(1H, brs), 7.15(1H, d, J=6.8Hz), 7.60(1H, t, J=7.9Hz), 7.82(1H, dd, J=1.1Hz, 8.6Hz), 8.97(1H, s) |
| 23 | 8-CF₃ | —CH₂CH=CH₂ | H | n = 1 | 4.13–4.19(2H, m), 5.21–5.38 (2H, m), 5.87–6.06(1H, m), 6.47(1H, brs), 7.75(1H, t, J=7.9Hz), 8.18(1H, d, J=7.3Hz), 8.51(1H, d, J=8.6Hz), 9.12(1H, s) |
| 24 | 8-Cl | —CH₂CH=CH₂ | H | n = 1 | 4.15–4.22(2H, m), 5.23–5.40 (2H, m), 5.90–6.09(1H, m), 6.45(1H, brs), 7.61(1H, dd, J=7.6Hz, 8.5Hz), 7.94(1H, dd, J=1.3Hz, 7.6Hz), 8.22(1H, dd, J=1.3Hz, 8.5Hz), 9.11(1H, s) |
| 25 | 8-C₂H₅ | —CH₂CH₂CH₃ | H | n = 1 | 1.03(3H, t, J=7.4Hz), 1.36 (3H, t, J=7.5Hz), 1.61–1.79 (2H, m), 3.26(2H, q, J=7.5Hz), 3.50(2H, q, J=5.9Hz), 6.39 (1H, brs), 7.55–7.67(2H, m), 8.12(1H, dd, J=2.0Hz, 7.9Hz), 9.00(1H, s) |
| 26 | 8-CH₃ | —CH₂CH₂CH₃ | H | n = 1 | 1.09(3H, t, J=7.4Hz), 1.70–1.81(2H, m), 2.86(3H, s), |

TABLE 1-continued

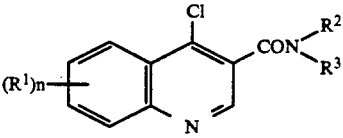

| Reference Example | R¹ | R² | R³ | | NMR (CDCl$_3$)δppm |
|---|---|---|---|---|---|
| | | | | | 3.51(2H, q, J=5.9Hz), 7.60–7.73(2H, m), 8.21(1H, d, J=7.1Hz), 8.98(1H, s) |
| 27 | 8-C$_2$H$_5$ | —CH$_2$C(CH$_3$)=CH$_2$ | H | n = 1 | 1.36(3H, t, J=7.5Hz), 1.85 (3H, s), 3.29(2H, q, J=7.5Hz), 4.10(2H, d, J=6.0Hz), 4.94 (1H, s), 5.01(1H, s), 6.53(1H, brs), 7.57–7.68(2H, m), 8.15(1H, dd, J=2Hz, 7.9Hz), 9.03(1H, s) |
| 28 | 8-OCH$_3$ | —CH$_2$-C$_6$H$_5$ | H | n = 1 | 4.06(3H, s), 6.23(2H, d, J=5.6Hz), 6.75(1H, brs), 7.13 (1H, d, J=6.9Hz), 7.30–7.44 (5H, m), 7.57(1H, t, J=8.5Hz), 7.78(1H, dd, J=1.1Hz, 8.6Hz), 8.98(1H, s) |
| 29 | 8-OCH$_3$ | —CH$_3$ | H | n = 1 | 3.11(3H, d, J=3.9Hz), 6.59 (1H, brs), 7.14(1H, d, J=7.8 Hz), 7.57(1H, t, J=8.5Hz), 7.77(1H, d, J=8.6Hz), 8.92(1H, s) |
| 30 | 8-C$_2$H$_5$ | —(2-methylphenyl) | H | n = 1 | 1.38(3H, t, J=7.5Hz), 2.37 (3H, s), 3.32(2H, q, J=7.5Hz), 7.10–7.33(4H, m), 7.60–7.72 (1H, m), 7.89(1H, brs), 8.04(1H, d, J=7.6Hz), 8.19(1H, d, J=7.8Hz), 9.17(1H, s) |
| 31 | 8-C$_2$H$_5$ | —CH$_3$ | H | n = 1 | 1.35(3H, t, J=7.5Hz), 3.09(3H, d, J=4.9Hz), 3.28(2H, q, J=7.5Hz), 6.42(1H, brs), 7.55–7.67(2H, m), 8.12(1H, dd, J=1.9Hz, 7.9Hz), 9.01(1H, s) |
| 32 | 8-OCH$_3$ | H | H | n = 1 | 4.11(3H, s), 7.21(1H, d, J=7.3Hz), 7.38(1H, brs), 7.66(1H, t, J=8.4Hz), 7.77(1H, brs), 7.88(1H, d, J=7.7Hz), 8.93(1H, s) |
| 33 | 8-C$_2$H$_5$ | —CH$_2$CF$_3$ | H | n = 1 | 1.36(3H, t, J=7.5Hz), 3.29(2H, t, J=7.5Hz), 4.12–4.29(2H, m), 7.58–7.70(2H, m), 8.14(1H, dd, J=1.9Hz, 8.0Hz), 9.02(1H, s) |
| 34 | 8-OCH$_3$ | —CH$_2$C(CH$_3$)=CH$_2$ | H | n = 1 | 1.86(3H, s), 4.10(3H, s), 4.11(2H, d, J=5.1Hz), 4.95(1H, s), 5.02(1H, s), 6.56(1H, brs), 7.15(1H, d, J=7.0Hz), 7.59(1H, t, J=8.5Hz), 7.80(1H, dd, J=1.1Hz, 8.6Hz), 8.99(1H, s) |
| 35 | 8-OCH$_3$ | —CH$_2$CF$_3$ | H | n = 1 | 4.08(3H, s), 4.13–4.30(2H, m), 7.12(1H, d, J=7.7Hz), 7.15(1H, brs), 7.54(1H, t, J=8.5Hz), 7.70(1H, d, J=8.5Hz), 8.85(1H, s) |

TABLE 1-continued

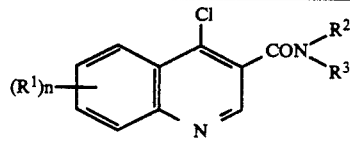

| Reference Example | $R^1$ | $R^2$ | $R^3$ | | NMR (CDCl$_3$)δppm |
|---|---|---|---|---|---|
| 36 | 8-OCH$_3$ | —CH$_2$—(cyclohexyl) | H | n = 1 | mp. 184–186° C.<br>solvent for recrystallization:<br>ethyl acetate-n-hexane<br>shape of crystals:<br>colorless needle-like crystals<br>form: free |
| 37 | 8-OCH$_3$ | —CH$_2$—(cyclopropyl) | H | n = 1 | mp. 152–153° C.<br>solvent for recrystallization: ethyl acetate<br>shape of crystals:<br>colorless needle-like crystals<br>form: free |
| 38 | H | —CH$_2$CH=CH$_2$ | H | n = 0 | mp. 181–184° C.<br>solvent for recrystallization:<br>ethanol-ethyl acetate-n-hexane<br>shape of crystals: pale brown powdered<br>form: free |
| 39 | 8-OCH$_3$ | —CH$_2$CH$_2$F | H | n = 1 | mp. 139–141° C.<br>solvent for recrystallization:<br>ethyl acetate-n-hexane<br>shape of crystals: brown powdered<br>form: free |
| 40 | 8-CH$_3$ | —CH$_2$—(cyclopropyl) | H | n = 1 | mp. 151.5–153° C.<br>solvent for recrystallization: ethyl acetate<br>shape of crystals:<br>colorless needle-like crystals<br>form: free |
| 41 | 8-OCH$_3$ | —CH$_2$CH$_2$OH | H | n = 1 | mp. 190–192° C. (decomposed)<br>solvent for recrystallization:<br>ethanol-ethyl acetate-n-hexane<br>shape of crystals: white powdered<br>form: free |

Example 1

0.3 G of N-(2-propenyl)-4-chloro-8-methoxyquinoline-3-carboxamide and 0.26 g of o-ethylaniline were dissolved in 20 ml of dioxane, and the reaction mixture was refluxed for five hours. After dioxane was distilled off, the residue was recrystallized from ethanol and n-hexane to give 0.2 g of N-(2-propenyl)-4-[(2-ethylphenyl)amino]-8-methoxyquinoline-3-carboxamide hydrochloride in the form of yellow powder. mp. 222° to 223° C. (decomposed)

In the same manner as in Example 1, there were prepared the compounds shown in Table 2 with the use of suitable starting materials.

TABLE 2

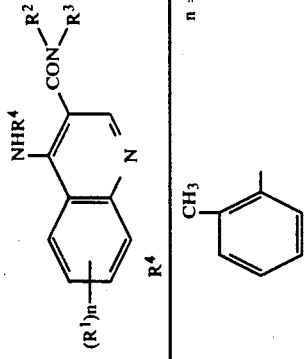

| Example | $R^1$ | $R^2$ | $R^3$ | $R^4$ | | |
|---|---|---|---|---|---|---|
| 2 | 8-OCH₃ | cyclohexyl | H | 2-CH₃-phenyl | n = 1 | mp. 168–171° C.<br>solvent for recrystallization: ethyl acetat-n-hexane<br>shape of crystals: white powdered<br>form: ¼ hydrate |
| 3 | 8-OCH₃ | CH₂=CHCH₂— | H | 2-CH₃-phenyl | n = 1 | mp. 231–232° C. (decomposed)<br>solvent for recrystallization: ethanol-ethyl acetate-n-hexane<br>shape of crystals: yellow powdered<br>form: hydrochloride |
| 4 | 8-OCH₃ | CH₂=CHCH₂— | H | 2-F-phenyl | n = 1 | mp. 232–233° C. (decomposed)<br>solvent for recrystallization: ethanol-ethyl acetate-n-hexane<br>shape of crystals: yellow powdered<br>form: hydrochloride |
| 5 | 8-OCH₃ | CH₂=CHCH₂— | H | 2-OCH₃-phenyl | n = 1 | mp. 257.5–258.5° C. (decomposed)<br>solvent for recrystallization: ethanol-ethyl acetate-n-hexane<br>shape of crystals: yellow powdered<br>form: hydrochloride.¼ hydrate |
| 6 | H | C₂H₅— | H | 2-CH₃-phenyl | n = 0 | mp. 192–193° C.<br>solvent for recrystallization: ethyl acetate-n-hexane<br>shape of crystals: pale yellow powdered<br>form: free |
| 7 | 8-OCH₃ | CH₂=CHCH₂— | H | 2-CH₃-6-F-phenyl | n = 1 | mp. 215–216° C. (decomposed)<br>solvent for recrystallization: ethanol-ethyl acetate-n-hexane<br>shape of crystals: pale yellow powdered<br>form: hydrochloride |

TABLE 2-continued structure:

| Example | R¹ | R² | R³ | R⁴ | | |
|---|---|---|---|---|---|---|
| 8 | 8-OCH₃ | CH₂=CHCH₂— | H | 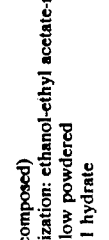 | n = 1 | mp. 239-240° C.<br>solvent for recrystallization: ethanol-ethyl acetate<br>shape of crystals: yellow powdered<br>form: free |
| 9 | 8-OCH₃ | CH₂=CHCH₂— | H |  | n = 1 | mp. 204-205° C.<br>solvent for recrystallization: ethyl acetate-n-hexane<br>shape of crystals: pale yellow powdered<br>form: free |
| 10 | 8-OCH₃ | CH₂=CHCH₂— | CH₂=CHCH₂— | 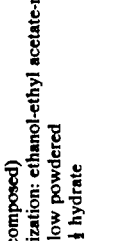 | n = 1 | mp. 182-183° C. (decomposed)<br>solvent for recrystallization: ethanol-ethyl acetate-n-hexane<br>shape of crystals: yellow powdered<br>form: hydrochloride.1 hydrate |
| 11 | 8-OCH₃ | CH₃O(CH₂)₂— | H |  | n = 1 | mp. 206-207° C.<br>solvent for recrystallization: ethanol-ethyl acetate-n-hexane<br>shape of crystals: white powdered<br>form: free |
| 12 | 8-OCH₃ | CH≡CCH₂— | H |  | n = 1 | mp. 237-238° C. (decomposed)<br>solvent for recrystallization: ethanol-ethyl acetate-n-hexane<br>shape of crystals: yellow powdered<br>form: hydrochloride.½ hydrate |
| 13 | H | CH₂=CHCH₂— | H |  | n = 1 | mp. 283-285° C.<br>solvent for recrystallization: ethanol-ethyl acetate<br>shape of crystals: pale yellow powdered<br>form: hydrochloride |

TABLE 2-continued

![Structure: quinoline with (R¹)n, NHR⁴, CON(R²)(R³) substituents]

| Example | R¹ | R² | R³ | R⁴ | |
|---|---|---|---|---|---|
| 14 | 8-OCH₃ | $C_2H_5CH-$<br>$\quad\;\;\;\;\;\;\;\;\vert$<br>$\quad\;\;\;\;\;\;\;\;CH_3$ | H | 2-methylphenyl (CH₃) | n = 1; mp. 252.5–253.5° C. (decomposed)<br>solvent for recrystallization: ethanol-ethyl acetate<br>shape of crystals: pale yellow powdered<br>form: hydrate |
| 15 | 8-OCH₃ | HO(CH₂)₃— | H | 2-methylphenyl | n = 1; mp. 182–184° C.<br>solvent for recrystallization: ethanol-ethyl acetate-n-hexane<br>shape of crystals: pale yellow powdered<br>form: free |
| 16 | 8-F | CH₂=CHCH₂— | H | 2-methylphenyl | n = 1; mp. 236.5–237.5° C.<br>solvent for recrystallization: ethanol-ethyl acetate-n-hexane<br>shape of crystals: brown needle-like crystals<br>form: free |
| 17 | 8-OCH₃ | cyclopropyl | H | 2-methylphenyl | n = 1; mp. 272–273° C. (decomposed)<br>solvent for recrystallization: ethanol-ethyl acetate<br>shape of crystals: pale yellow powdered<br>form: hydrochloride |
| 18 | 8-OC₂H₅ | CH₂=CHCH₂— | H | 2-methylphenyl | n = 1; mp. 177–178° C.<br>solvent for recrystallization: ethyl acetate-n-hexane<br>shape of crystals: pale brown needle-like crystals<br>form: free |
| 19 | 7-Cl, 8-OCH₃ | CH₂=CHCH₂— | H | 2-methylphenyl | n = 2; mp. 215–216° C.<br>solvent for recrystallization: ethyl acetate-n-hexane<br>shape of crystals: white powdered<br>form: free |

TABLE 2-continued

Structure: quinoline with (R¹)n, NHR⁴, CONR²R³ substituents

| Example | R¹ | R² | R³ | R⁴ | |
|---|---|---|---|---|---|
| 20 | 5-CH₃, 8-OCH₃ | CH₂=CHCH₂— | H | 2-CH₃-phenyl | n = 2; mp. 250-251° C. (decomposed); solvent for recrystallization: ethanol-ethyl acetate-n-hexane; shape of crystals: pale yellow powdered; form: hydrochloride |
| 21 | 8-SCH₃ | CH₂=CHCH₂— | H | 2-CH₃-phenyl | n = 1; mp. 263.5-265° C. (decomposed); solvent for recrystallization: ethanol-ethyl acetate-n-hexane; shape of crystals: yellow powdered; form: hydrochloride |
| 22 | 8-OCH₃ | CH₂=CHCH₂— | H | 2-SCH₃-phenyl | n = 1; 242-243° C. (decomposed); solvent for recrystallization: ethanol-ethyl acetate-n-hexane; shape of crystals: yellow powdered; form: hydrochloride |
| 23 | 8-OCH₃ | CH₂=CHCH₂— | H | 2-CH(CH₃)₂-phenyl | n = 1; mp. 228-229° C. (decomposed); solvent for recrystallization: ethanol-ethyl acetate; shape of crystals: pale yellow powdered; form: hydrochloride |
| 24 | 8-OCH₃ | CH₂=CHCH₂— | H | 2-OC₂H₅-phenyl | n = 1; mp. 216-218° C. (decomposed); solvent for recrystallization: ethanol-ethyl acetate; shape of crystals: yellow powdered; form: hydrochloride |
| 25 | 8-OCH₃ | CH≡CCH₂— | H | 2-C₂H₅-phenyl | n = 1; mp. 218-220° C.; solvent for recrystallization: ethyl acetate-n-hexane; shape of crystals: pale yellow powdered; form: free |

TABLE 2-continued

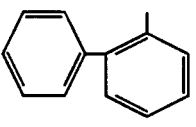

| Example | R¹ | R² | R³ | R⁴ | | |
|---|---|---|---|---|---|---|
| 26 | 8-OCH₃ | CH₂=CHCH₂— | H | (o-COCH₃-phenyl) | n = 1 | mp. 204-206° C. (decomposed) solvent for recrystallization: ethanol-ethyl acetate shape of crystals: pale yellow powdered form: hydrochloride |
| 27 | 8-OCH₃ | CH₂=CHCH₂— | H | (o-phenyl-phenyl) | n = 1 | mp. 225-226.5° C. (decomposed) solvent for recrystallization: ethanol-ethyl acetate-n-hexane shape of crystals: pale yellow powdered form: hydrochloride |
| 28 | 8-OCH₃ | CH₂=CHCH₂— | H | (o-CN-phenyl) | n = 1 | mp. 245-246° C. (decomposed) solvent for recrystallization: ethanol-ethyl acetate shape of crystals: pale yellow powdered form: hydrochloride.1 hydrate |
| 29 | 8-OCH₃ | CH₂=CHCH₂— | H | (o-Br-phenyl) | n = 1 | 229.5-230.5° C. (decomposed) solvent for recrystallization: ethanol-ethyl acetate-n-hexane shape of crystals: pale yellow powdered form: hdrochloride |
| 30 | 8-OCH₃ | CH₂=CHCH₂— | H | (o-SC₂H₅-phenyl) | n = 1 | mp. 246.5-247.5° C. (decomposed) solvent for recrystallization: ethanol-ethyl acetate-n-hexane shape of crystals: pale yellow powdered form: hydrochloride.½ hydrate |

TABLE 2-continued

[Structure: quinoline with (R¹)ₘ, R⁴, NHR⁴, CONR²R³ substituents]

| Example | R¹ | R² | R³ | R⁴ | | |
|---------|-----|-----|-----|-----|---|---|
| 31 | 8-OCH₃ | cyclopropyl | H | 2-C₂H₅-phenyl | n = 1 | mp. 251–252° C. (decomposed) solvent for recrystallization: ethanol-ethyl acetate-n-hexane shape of crystals: pale yellow powdered form: hydrochloride |
| 32 | 8-OCH₃ | CH₂=CHCH₂— | H | 3-C₂H₅-phenyl | n = 1 | mp. 194–196° C. (decomposed) solvent for recrystallization: ethanol-ethyl acetate-n-hexane shape of crystals: pale yellow powdered form: hydrochloride.1 hydrate |
| 33 | 8-OCH₃ | CH₂=CHCH₂— | H | 2-(S(=O)CH₃)-phenyl | n = 1 | mp. 190–192° C. (decomposed) solvent for recrystallization: ethanol-ethyl acetate-n-hexane shape of crystals: pale yellow powdered form: hydrochloride |
| 34 | 8-OCH₃ | CH₂=CHCH₂— | H | 2-COOC₂H₅-phenyl | n = 1 | mp. 207–209° C. (decomposed) solvent for recrystallization: ethanol-ethyl acetate-n-hexane shape of crystals: pale yellow powdered form: hydrochloride |
| 35 | 8-OCH₃ | CH₂=CHCH₂— | H | 2-Cl-phenyl | n = 1 | mp. 238.8–239.5° C. (decomposed) solvent for recrystallization: ethanol-ethyl acetate-n-hexane shape of crystals: pale yellow powdered form: hydrochloride |
| 36 | 8-OCH₃ | CH₂=CHCH₂— | H | 2-S(CH₂)₂CH₃-phenyl | n = 1 | mp. 206–207° C. (decomposed) solvent for recrystallization: ethanol-ethyl acetate-n-hexane shape of crystals: pale yellow powdered form: hydrochloride |

TABLE 2-continued

| Example | R¹ | R² | R³ | R⁴ | | |
|---|---|---|---|---|---|---|
| 37 | 8-OCH₃ | CH₂=CHCH₂— | H | SCH₂CH=CH₂ phenyl(o-) | n = 1 | 205.5–207° C. (decomposed) solvent for recrystallization: ethanol-ethyl acetate-n-hexane shape of crystals: pale yellow granular form: hydrochloride |
| 38 | 8-OCH₃ | CH₂=CHCH₂— | H | CH₂CH₂CH₃ phenyl(o-) | n = 1 | mp. 232.5–233.5° C. (decomposed) solvent for recrystallization: ethanol-ethyl acetate-n-hexane shape of crystals: pale yellow powdered form: hydrochloride.½ hydrate |
| 39 | 8-OCH₃ | CH₂=CHCH₂— | H | S(CH₂)₅CH₃ phenyl(o-) | n = 1 | mp. 187–189° C. (decomposed) solvent for recrystallization: ethanol-ethyl acetate-n-hexane shape of crystals: pale yellow powdered form: hydrochloride |
| 40 | 8-OCH₃ | CH₂=CHCH₂— | H | 2,6-dimethylphenyl | n = 1 | mp. 249.5–250.5° C. (decomposed) solvent for recrystallization: ethanol-ethyl acetate-n-hexane shape of crystals: colorless needle-like crystals form: free |
| 41 | 8-OCH₃ | CH₂=CHCH₂— | H | S(CH₂)₃CH₃ phenyl | n = 1 | mp. 175–176° C. solvent for recrystallization: ethyl acetate-n-hexane shape of crystals: pale yellow scaly form: free |

TABLE 2-continued

![structure: quinoline with (R¹)n, NHR⁴, CONR²R³]

| Example | R¹ | R² | R³ | R⁴ | |
|---|---|---|---|---|---|
| 42 | 8-OCH₃ | CH₂=CHCH₂— | H | 2-(CH₃S)phenyl | n = 1; mp. 203–204° C. (decomposed); solvent for recrystallization: ethanol-ethyl acetate-n-hexane; shape of crystals: yellow powdered; form: hydrochloride |
| 43 | 8-OCH₃ | CH₂=CHCH₂— | H | 2-benzoylphenyl | n = 1; mp. 256–257° C. (decomposed); solvent for recrystallization: ethanol; shape of crystals: pale yellow powdered; form: hydrochloride |
| 44 | 8-OCH₃ | CH₂=CHCH₂— | H | 5,6,7,8-tetrahydronaphthyl | n = 1; mp. 236–237° C. (decomposed); solvent for recrystallization: ethanol-ethyl acetate-n-hexane; shape of crystals: brown powdered; form: hydrochloride |
| 45 | 8-OCH₃ | CH₂=CHCH₂— | H | 2-(CH₂=C(CH₃)—)phenyl | n = 1; mp. 230–231° C. (decomposed); solvent for recrystallization: ethanol-ethyl acetate-n-hexane; shape of crystals: pale yellow powdered; form: hydrochloride |
| 46 | 8-OCH₃ | CH₂=CHCH₂— | H | 2-(CH₂CH₂OH)phenyl | n = 1; mp. 163–165° C. (decomposed); solvent for recrystallization: ethanol-ethyl acetate-n-hexane; shape of crystals: pale brown needle-like crystals; form: hydrochloride |

TABLE 2-continued

| Example | R¹ | R² | R³ | R⁴ | |
|---|---|---|---|---|---|
| 47 | 8-OCH₃ | CH₂=CHCH₂— | H | 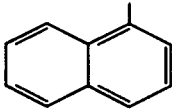 | n = 1  mp. 264-265° C. (decomposed)  solvent for recrystallization: ethanol-ethyl acetate  shape of crystals: yellow powdered  form: hydrochloride |
| 48 | 8-OCH₃ | CH₂=CHCH₂— | H | 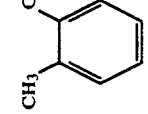 | n = 1  mp. 222-224° C. (decomposed)  solvent for recrystallization: ethanol-ethyl acetate-n-hexane  shape of crystals: yellow powdered  form: hydrochloride.½ hydrate |
| 49 | 8-OCH₃ | CH₂=CHCH₂— | H | 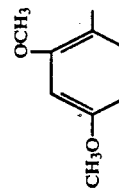 | n = 1  mp. 138-140° C. (decomposed)  solvent for recrystallization: ethanol-ethyl acetate-n-hexane  shape of crystals: yellowy brown powdered  form: hydrochloride.1 hydrate |
| 50 | 8-OCH₃ | CH₂=CHCH₂— | H | 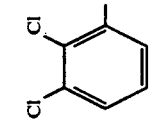 | n = 1  mp. 242-243.5° C. (decomposed)  solvent for recrystallization: ethanol-ethyl acetate-n-hexane  shape of crystals: yellow powdered  form: hydrochloride |
| 51 | 8-OCH₃ | CH₂=CHCH₂— | H | 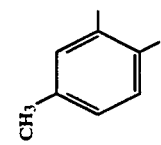 | n = 1  mp. 221-222° C. (decomposed)  solvent for recrystallization: ethyl acetate  shape of crystals: brown granular  form: hydrochloride |

TABLE 2-continued

![Structure: quinoline with (R¹)ₙ on benzo ring, NHR⁴ at position 4, CON(R²)(R³) at position 3]

| Example | R¹ | R² | R³ | R⁴ | CONR²R³ side | n | Properties |
|---|---|---|---|---|---|---|---|
| 52 | 8-OCH₃ | CH₂=CHCH₂— | H | 2-methylphenyl | CH₂CH₂OCOCH₃ | 1 | mp. 160–161° C.<br>solvent for recrystallization: ethyl acetate-n-hexane<br>shape of crystals: pale yellow powdered<br>form: free |
| 53 | 8-CH₃ | CH₂=CHCH₂— | H | 2-ethylphenyl | C₂H₅ | 1 | mp. 149–150° C.<br>solvent for recrystallization: ethyl acetate-n-hexane<br>shape of crystals: colorless needle-like crystals<br>form: free |
| 54 | 8-OCH₃ | CH₂=CHCH₂— | H | 2-butylphenyl | (CH₂)₃CH₃ | 1 | mp. 208–209° C. (decomposed)<br>solvent for recrystallization: ethanol-ethyl acetate-n-hexane<br>shape of crystals: yellow powdered<br>form: hydrochloride |
| 55 | 8-C₂H₅ | CH₂=CHCH₂— | H | 2-ethylphenyl | C₂H₅ | 1 | mp. 117–118° C.<br>solvent for recrystallization: ethyl acetate-n-hexane<br>shape of crystals: yellow needle-like crystals<br>form: free |
| 56 | 8-C₂H₅ | CH₂=CHCH₂— | H | 2-isopropylphenyl | CH(CH₃)₂ | 1 | mp. 176–178° C.<br>solvent for recrystallization: ethyl acetate<br>shape of crystals: pale yellow powdered<br>form: hydrochloride |
| 57 | 8-C₂H₅ | CH₂=CHCH₂— | H | 2-methylphenyl | CH₃ | 1 | mp. 231.5–232.5° C.<br>solvent for recrystallization: ethanol-ethyl acetate-n-hexane<br>shape of crystals: pale yellow powdered<br>form: hydrochloride |

TABLE 2-continued

![structure: quinoline with (R¹)ₙ on benzene ring, NHR⁴ at 4-position, CON(R²)(R³) at 3-position, N in ring]

| Example | R¹ | R² | R³ | R⁴ | | |
|---|---|---|---|---|---|---|
| 58 | 8-CH₃ | CH₂=CHCH₂— | H | 2-CH(CH₃)₂-phenyl | n = 1 | mp. 252.5-254.5° C. solvent for recrystallization: ethanol-ethyl acetate-n-hexane shape of crystals: pale yellow powdered form: hydrochloride |
| 59 | 8-CH₃ | CH₂=CHCH₂— | H | 2-CH₃-phenyl | n = 1 | mp. 234-235° C. solvent for recrystallization: ethanol-ethyl acetate-n-hexane shape of crystals: pale yellow powdered form: hydrochloride |
| 60 | 8-CH₂OCOCH₃ | CH₂=CHCH₂— | H | 2-C₂H₅-phenyl | n = 1 | mp. 114-115° C. solvent for recrystallization: ethyl acetate-n-hexane shape of crystals: pale yellow powdered form: free |
| 61 | 8-CH₂OH | CH₂CHCH₂— | H | 2-C₂H₅-phenyl | n = 1 | mp. 151-152° C. solvent for recrystallization: ethyl acetate-n-hexane shape of crystals: pale yellow powdered form: free |
| 62 | 8-CH₂OH | CH₂=CHCH₂— | H | 2-CH₃-phenyl | n = 1 | mp. 179-181° C. solvent for recrystallization: ethyl acetate-n-hexane shape of crystals: pale yellow powdered form: free |
| 63 | 8-OCH₃ | CH₂=CHCH₂— | H | 2-CH₃-5-F-phenyl | n = 1 | mp. 223.5-224° C. (decomposed) solvent for recrystallization: ethanol-ethyl acetate-n-hexane shape of crystals: yellow powdered form: hydrochloride |

TABLE 2-continued

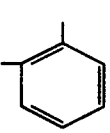

| Example | R¹ | R² | R³ | R⁴ | | |
|---|---|---|---|---|---|---|
| 64 | 8-CHCH₃<br>\|<br>OH | CH₂=CHCH₂— | H | 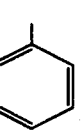 | n = 1 | mp. 131–132° C.<br>solvent for recrystallization: ethyl acetate-n-hexane<br>shape of crystals: pale yellow powdered<br>form: free |
| 65 | 8-CH(CH₃)₂ | CH₂=CHCH₂— | H | 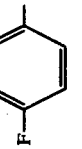 | n = 1 | mp. 228–230° C.<br>solvent for recrystallization: ethyl acetate-n-hexane<br>shape of crystals: yellow granular<br>form: hydrochloride.½ hydrate |
| 66 | 8-C₂H₅ | CH₂=CHCH₂— | H | 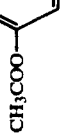 | n = 1 | mp. 220–223° C.<br>solvent for recrystallization: ethanol-ethyl acetate-n-hexane<br>shape of crystals: pale yellow powdered<br>form: hydrochloride |
| 67 | 8-OCH₃ | CH₂=CHCH₂— | H | 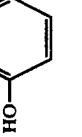 | n = 1 | mp. 238–239° C. (decomposed)<br>solvent for recrystallization: ethanol-ethyl acetate-n-hexane<br>shape of crystals: yellow powdered<br>form: hydrochloride |
| 68 | 8-OCH₃ | CH₂=CHCH₂— | H |  | n = 1 | mp. 241.5–242.5° C.<br>solvent for recrystallization: ethanol-ethyl acetate-n-hexane<br>shape of crystals: pale yellow powdered<br>form: free |
| 69 | 8-C₂H₅ | CH₂=CHCH₂— | H |  | n = 1 | mp. 220–221° C.<br>solvent for recrystallization: ethanol-ethyl acetate-n-hexane<br>shape of crystals: pale yellow powdered<br>form: hydrochloride |

TABLE 2-continued

![General structure: quinoline with (R¹)n, NHR⁴ at 4-position, CONR²R³ at 3-position, R⁴ substituent]

| Example | R¹ | R² | R³ | R⁴ | | |
|---|---|---|---|---|---|---|
| 70 | 8-OCH₃ | CH₂=CHCH₂— | H | 4-hydroxyphenyl | n = 1 | mp. 254–255° C. (decomposed)<br>solvent for recrystallization: ethanol-ethyl acetate<br>shape of crystals: brown powder<br>form: hydrochloride |
| 71 | 8-OCH₃ | C₂H₅— | H | 2-ethylphenyl | n = 1 | mp. 234–235° C. (decomposed)<br>solvent for recrystallization: ethanol-ethyl acetate-n-hexane<br>shape of crystals: pale yellow powdered<br>form: hydrochloride |
| 72 | 8-C₂H₅ | C₂H₅— | H | 2-methylphenyl | n = 1 | mp. 251–253° C.<br>solvent for recrystallization: ethanol-ethyl acetate-n-hexane<br>shape of crystals: pale brown powdered<br>form: hydrochloride |
| 73 | 8-OCH₃ | C₂H₅— | H | 2-methylphenyl | n = 1 | mp. 254.5–255.5° C. (decomposed)<br>solvent for recrystallization: ethanol-ethyl acetate-n-hexane<br>shape of crystals: pale yellow powdered<br>form: hydrochloride |
| 74 | 8-C₂H₅ | CH₂=CHCH₂— | H | 3-methyl-4-hydroxyphenyl | n = 1 | mp. 186–187° C.<br>solvent for recrystallization: ethyl acetate-n-hexane<br>shape of crystals: yellow granular<br>form: free |
| 75 | 8-OCH₃ | CH₃(CH₂)₂— | H | 2-ethylphenyl | n = 1 | mp. 91–93° C.<br>solvent for recrystallization: ethanol-ethyl acetate-n-hexane<br>shape of crystals: yellow powdered<br>form: hydrochloride |

TABLE 2-continued

![Structure: quinoline with (R¹)ₙ on benzene ring, R⁴ at 4-position, NHR⁴ and CONR²R³ groups]

| Example | R¹ | R² | R³ | R⁴ | | |
|---|---|---|---|---|---|---|
| 76 | 8-C₂H₅ | CH₂=CHCH₂— | H | SCH₂CH₂CH₃ phenyl(o-) | n = 1 | mp. 212–213° C.<br>solvent for recrystallization: ethanol-ethyl acetate-n-hexane<br>shape of crystals: yellow scaly<br>form: hydrochloride |
| 77 | 8-C₂H₅ | CH₃(CH₂)₂— | H | o-CH₃-phenyl | n = 1 | mp. 223–224.5° C.<br>solvent for recrystallization: ethanol-ethyl acetate-n-hexane<br>shape of crystals: pale yellow powdered<br>form: hydrochloride |
| 78 | 8-OCH₃ | CH₃(CH₂)₂— | H | o-CH₃-phenyl | n = 1 | mp. 117–118° C. (decomposed)<br>solvent for recrystallization: ethanol-ethyl acetate-n-hexane<br>shape of crystals: yellow needle-like crystals<br>form: hydrochloride |
| 79 | 8-Cl | CH₂=CHCH₂— | H | o-C₂H₅-phenyl | n = 1 | mp. 243–245° C.<br>solvent for recrystallization: ethanol-ethyl acetate-n-hexane<br>shape of crystals: yellow powder<br>form: hydrochloride |
| 80 | 8-CF₃ | CH₂=CHCH₂— | H | o-C₂H₅-phenyl | n = 1 | mp. 155–156° C.<br>solvent for recrystallization: ethyl acetate-n-hexane<br>shape of crystals: pale yellow needle-like crystals<br>form: free |
| 81 | 8-Cl | CH₂=CHCH₂— | H | o-CH₃-phenyl | n = 1 | mp. 237–239° C. (decomposed)<br>solvent for recrystallization: ethanol-ethyl acetate-n-hexane<br>shape of crystals: yellow powdered<br>form: hydrochloride |

TABLE 2-continued

Structure: quinoline with (R¹)ₘ on benzene ring, NHR⁴ and CON(R²)(R³) substituents

| Example | R¹ | R² | R³ | R⁴ | Notes |
|---------|-----|-----|-----|-----|-------|
| 82 | 8-CF₃ | CH₂=CHCH₂— | H | 2-CH₃-C₆H₄ | n = 1; mp. 156.5-157.5° C.; solvent for recrystallization: ethyl acetate-n-hexane; shape of crystals: pale yellow needle-like crystals; form: free |
| 83 | 8-CH₃ | CH₃(CH₂)₂— | H | 2-C₂H₅-C₆H₄ | n = 1; mp. 177-179° C. (decomposed); solvent for recrystallization: ethanol-ethyl acetate-n-hexane; shape of crystals: pale yellow powdered; form: hydrochloride |
| 84 | 8-C₂H₅ | CH₂=CCH₂—(—CH₃) | H | 2-CH₃-C₆H₄ | n = 1; mp. 190-191° C.; solvent for recrystallization: ethanol-ethyl acetate-n-hexane; shape of crystals: yellow scaly; form: hydrochloride |
| 85 | 8-OCH₃ | C₂H₅— | H | 2-CH(CH₃)₂-C₆H₄ | n = 1; mp. 242-243° C. (decomposed); solvent for recrystallization: ethanol-ethyl acetate-n-hexane; shape of crystals: pale yellow scaly; form: hydrochloride |
| 86 | 8-CH₃ | CH₂=CHCH₂— | H | 2-CH₂CH₂CH₃-C₆H₄ | n = 1; mp. 131.5-132.5° C.; solvent for recrystallization: ethyl acetate-n-hexane; shape of crystals: pale yellow needle-like crystals; form: free |
| 87 | 8-OCH₃ | C₆H₅CH₂— | H | 2-C₂H₅-C₆H₄ | n = 1; mp. 229-230° C. (decomposed); solvent for recrystallization: ethanol-ethyl acetate-n-hexane; shape of crystals: pale yellow powdered; form: hydrochloride |

TABLE 2-continued

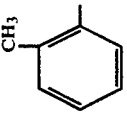

| Example | R¹ | R² | R³ | R⁴ | n | |
|---|---|---|---|---|---|---|
| 88 | 8-OCH₃ | CH₃— | H | 2-C₂H₅-phenyl | n = 1 | mp. 252-252.5° C. (decomposed) solvent for recrystallization: ethanol-ethyl acetate-n-hexane shape of crystals: pale yellow powdered form: hydrochloride |
| 89 | 8-OCH₃ | C₆H₅CH₂— | H | 2-CH₃-phenyl | n = 1 | mp. 251-252° C. (decomposed) solvent for recrystallization: ethanol-ethyl acetate-n-hexane shape of crystals: yellow powdered form: hydrochloride |
| 90 | 8-OCH₃ | CH₃— | H | 2-CH₃-phenyl | n = 1 | mp. 270-271° C. (decomposed) solvent for recrystallization: ethanol-ethyl acetate-n-hexane shape of crystals: pale yellow powdered form: hydrochloride |
| 91 | 8-C₂H₅ | CH₂=CCH₂—  \|  CH₃ | H | 2-C₂H₅-phenyl | n = 1 | mp. 96-97° C. solvent for recrystallization: ethyl acetate-n-hexane shape of crystals: pale yellow needle-like crystals form: free |
| 92 | 8-C₂H₅ | CH₃— | H | 2-CH₃-phenyl | n = 1 | mp. 242-244° C. solvent for recrystallization: ethanol-ethyl acetate-n-hexane shape of crystals: colorless prism-like crystals form: hydrochloride |
| 93 | 8-Cl | CH₂=CHCH₂— | H | 2-CH(CH₃)₂-phenyl | n = 1 | mp. 258-260° C. solvent for recrystallization: ethanol-ethyl acetate-n-hexane shape of crystals: yellow powdered form: hydrochloride |

TABLE 2-continued

Structure: quinoline with (R¹)ₙ, NHR⁴, and CON(R²)(R³) substituents

| Example | R¹ | R² | R³ | R⁴ | |
|---------|------|------|------|------|------|
| 94 | 8-C₂H₅ | CH₃ (phenyl) | H | CH₃ (o-tolyl) | n = 1; mp. 259-261° C.; solvent for recrystallization: ethanol-ethyl acetate-n-hexane; shape of crystals: yellow powdered; form: hydrochloride |
| 95 | 8-OCH₃ | H | H | CH₃ (o-tolyl) | n = 1; mp. 258-260° C. (decomposed); solvent for recrystallization: ethanol-n-hexane; shape of crystals: pale yellow needle-like crystals; form: hydrochloride |
| 96 | 8-OCH₃ | H | H | C₂H₅ (o-tolyl) | n = 1; mp. 225-227° C. (decomposed); solvent for recrystallization: ethanol-n-hexane; shape of crystals: pale yellow powdered; form: hydrochloride |
| 97 | 8-C₂H₅ | C₂H₅ | H | C₂H₅ (o-tolyl) | n = 1; mp. 125.5-126° C.; solvent for recrystallization: ethyl acetate-n-hexane; shape of crystals: pale yellow needle-like crystals; form: free |

TABLE 2-continued

![structure: quinoline with (R¹)n, NHR⁴, CONR²R³, R⁴ substituent]

| Example | R¹ | R² | R³ | R⁴ | |
|---|---|---|---|---|---|
| 98 | 8-OCH₃ | CH₂=CCH₂—<br>    |<br>    CH₃ | H | ![o-tolyl C₂H₅] | mp. 235-236° C. (decomposed)<br>solvent for recrystallization: ethanol-ethyl acetate-n-hexane<br>shape of crystals: yellowy brown powdered<br>form: hydrochloride.½ hydrate |
| 99 | 8-C₂H₅ | CF₃CH₂— | H | ![o-tolyl CH₃] | n = 1  mp. 177.5-179° C.<br>solvent for recrystallization: ethyl acetate-n-hexane<br>shape of crystals: pale yellow needle-like crystals<br>form: free |
| 100 | 8-OCH₃ | CF₃CH₂— | H | ![o-tolyl C₂H₅] | n = 1  mp. 214-215° C. (decomposed)<br>solvent for recrystallization: ethanol-ethyl acetate-n-hexane<br>shape of crystals: yellow powdered<br>form: hydrochloride.½ hydrate |
| 101 | 8-OCH₃ | CH₂=CCH₂—<br>    |<br>    CH₃ | H | ![o-tolyl CH₃] | n = 1  227-228° C. (decomposed)<br>solvent for recrystallization: ethanol-ethyl acetate-n-hexane<br>shape of crystals: yellow powdered<br>form: hydrochloride |

TABLE 2-continued

[Structure: quinoline with $(R^1)_m$ on benzene ring, $NHR^4$ at 4-position, $CON(R^2)(R^3)$ at 3-position]

| Example | $R^1$ | $R^2$ | $R^3$ | $R^4$ | | |
|---|---|---|---|---|---|---|
| 102 | 8-OCH$_3$ | CF$_3$CH$_2$— | H | 2-methylphenyl (CH$_3$) | n = 1 | mp. 233–235° C. (decomposed)<br>solvent for recrystallization: ethanol-ethyl acetate-n-hexane<br>shape of crystals: pale yellow powdered<br>form: hydrochloride |
| 103 | 8-SCH$_3$ | CH$_2$=CHCH$_2$— | H | 2-ethylphenyl (C$_2$H$_5$) | n = 1 | mp. 180–183° C.<br>solvent for recrystallization: ethanol-ethyl acetate-n-hexane<br>shape of crystals: brown powdered<br>form: hydrochloride |
| 104 | 8-OCH$_3$ | cyclohexylmethyl (CH$_2$-cyclohexyl) | H | 2-ethylphenyl (C$_2$H$_5$) | n = 1 | mp. 160.5–161.5° C.<br>solvent for recrystallization: ethyl acetate-n-hexane<br>shape of crystals: white powdered<br>form: free |
| 105 | 8-OCH$_3$ | cyclohexylmethyl (CH$_2$-cyclohexyl) | H | 2-methylphenyl (CH$_3$) | n = 1 | mp. 229.5–230° C. (decomposed)<br>solvent for recrystallization: ethanol-ethyl acetate-n-hexane<br>shape of crystals: yellow powdered<br>form: hydrochloride |
| 106 | 8-OCH$_3$ | CH$_2$=CHCH$_2$O— | H | 2-ethylphenyl (C$_2$H$_5$) | n = 1 | mp. 223–225° C. (decomposed)<br>solvent for recrystallization: ethanol-ethyl acetate-n-hexane<br>shape of crystals: yellow powdered<br>form: hydrochloride.½ hydrate |
| 107 | 8-Cl | CH$_2$=CHCH$_2$— | H | 2-propylphenyl (CH$_2$CH$_2$CH$_3$) | n = 1 | mp. 240–242° C.<br>solvent for recrystallization: ethanol-ethyl acetate-n-hexane<br>shape of crystals: yellow powdered<br>form: hydrochloride |

TABLE 2-continued

| Example | R¹ | R² | R³ | R⁴ | | |
|---|---|---|---|---|---|---|
| 108 | 8-OCH₃ | HOCH₂CH₂— | H | o-C₂H₅-phenyl | n = 1 | mp. 202–204° C. (decomposed) solvent for recrystallization: ethanol-ethyl acetate-n-hexane shape of crystals: yellow powdered form: hydrochloride ½ hydrate |
| 109 | 8-CH₂OCOCH₃ | CF₃CH₂— | H | o-C₂H₅-phenyl | n = 1 | mp. 176–178° C. solvent for recrystallization: ethyl acetate-n-hexane shape of crystals: white powdered form: free |
| 110 | 8-CH₂OH | CF₃CH₂— | H | o-C₂H₅-phenyl | n = 1 | mp. 189.5–190.5° C. solvent for recrystallization: ethyl acetate-n-hexane shape of crystals: pale brown powdered form: free |
| 111 | 8-OCH₃ | FCH₂CH₂— | H | o-C₂H₅-phenyl | n = 1 | mp. 201–202° C. (decomposed) solvent for recrystallization: ethyl acetate-n-hexane shape of crystals: yellow powdered form: hydrochloride |
| 112 | 8-OCH₃ | cyclopropyl-CH₂— | H | o-C₂H₅-phenyl | n = 1 | mp. 192.5–194° C. solvent for recrystallization: ethyl acetate-n-hexane shape of crystals: colorless needle-like crystals form: free |
| 113 | 8-OCH₃ | cyclopropyl-CH₂— | H | o-CH₃-phenyl | n = 1 | mp. 165–170° C. solvent for recrystallization: ethanol-ethyl acetate-n-hexane shape of crystals: yellow needle-like crystals form: free |

TABLE 2-continued

| Example | R¹ | R² | R³ | R⁴ | | |
|---|---|---|---|---|---|---|
| 114 | 8-CH₃ | cyclopropyl-CH₂— | H | 2-C₂H₅-phenyl | n = 1 | mp. 128–129° C.<br>solvent for recrystallization: ethyl acetate-n-hexane<br>shape of crystals: pale yellow needle-like crystals<br>form: free |

Pharmacological Test (a) Stomach-Acid Secretion Inhibitory Action on Rats

Testing Method

After each of Wistar-type male rats was let abstain from food for 24 hours, the pylorus thereof was bound while the rat was paralyzed with urethane (1.5 g/kg s.c.), and a stomach perfusion cannula was inserted into the rat stomach. The rat stomach was perfused with a physiological salt solution through an oral catheter. The amount of stomach-acid secretion was measured by titrating the total acidity and pH of the perfusion solution. As an acid secretion stimulant, 1 mg/kg/hr of histamine dihydrochloride was continuously injected through the femoral vein to accelerate the acid secretion. Then, the effects of a variety of compounds were studied.

Each of test compounds as dissolved in dimethylformamide was intravenously administered to the rat in each of dosages of 0.3, 1, 3, 10 and 30 mg/kg through talc-vein.

There was calculated an inhibition percentage of acid secretion with respect to acid secretion before administration of each of the test compounds. An $ED_{50}$ value was calculated from the inhibition percentage with respect to each dosage according to a probit method. The results are shown in Table 3.

| No. | Test Compounds — Name of Compound |
|---|---|
| 1 | N-2-propenyl-8-methoxy-4-[(2-methylphenyl)amino]quinoline-3-carboxamide hydrochloride |
| 2 | N-2-propenyl-4-[(2-ethylphenyl)amino]-8-methoxyquinoline-3-carboxamide hydrochloride |
| 3 | N-2-propenyl-4-[(2-isopropylphenyl)amino]-8-methoxyquinoline-3-carboxamide hydrochloride |
| 4 | N-2-propenyl-4-[(2-ethylthiophenyl)amino]-8-methoxy-quinoline-3-carboxamide hydrochloride.½ hydrate |
| 5 | N-2-propenyl-8-methoxy-4-[(2-propylthiophenyl)amino]quinoline-3-carboxamide hydrochloride |
| 6 | N-2-propenyl-8-methoxy-4-[(2-propylphenyl)amino]quinoline-3-carboxamide hydrochloride.½ hydrate |
| 7 | N-2-propenyl-8-methoxy-4-[(5,6,7,8-tetrahydro-1-naphtyl)amino] quinoline-3-carboxamide hydrochloride |
| 8 | N-2-propenyl-4-[(2-ethylphenyl)amino]-8-methyl-quinoline-3-carboxamide |
| 9 | N-2-propenyl-8-ethyl-4-[(2-isopropylphenyl)amino]quinoline-3-carboxamide hydrochloride |
| 10 | N-2-propenyl-8-ethyl-4-[(2-methylphenyl)amino]quinoline-3-carboxamide hydrochloride |
| 11 | N-2-propenyl-4-[(2-isopropylphenyl)amino]-8-methylquinoline-3-carboxamide hydrochloride |
| 12 | N-2-propenyl-8-methyl-4-[(2-methylphenyl)amino]quinoline-3-carboxamide hydrochloride |
| 13 | N-2-propenyl-8-acetyloxymethyl-4-[(2-ethylphenyl)amino]quinoline-3-carboxamide |
| 14 | N-2-propenyl-4-[(2-ethylphenyl)]amino-8-hydroxymethylquinoline-3-carboxamide |
| 15 | N-2-propenyl-8-ethyl-4-[(4-fluoro-2-methylphenyl)amino]quinoline-3-carboxamide hydrochloride |
| 16 | N-2-propenyl-4-[(4-acetyloxy-2-methylphenyl)amino]-8-ethylquinoline-3-carboxamide hydrochloride |
| 17 | N-ethyl-4-[(2-ethylphenyl)amino]-8-methoxyquinoline-3-carboxamide hydrochloride |
| 18 | N-ethyl-4-[(2-methylphenyl)amino]-8-ethylquinoline-3-carboxamide hydrochloride |
| 19 | N-ethyl-8-methoxy-4-[(2-methylphenyl)amino]quinoline-3-carboxamide hydrochloride |
| 20 | N-propyl-8-methoxy-4-[(2-ethylphenyl)amino]quinoline-3-carboxamide hydrochloride |
| 21 | N-2-propenyl-8-ethyl-4-[(2-propylthiophenyl)amino]quinoline-3-carboxamide hydrochloride |
| 22 | N-2-propenyl-8-chloro-4-[(2-ethylphenyl)amino]-quinoline-3-carboxamide hydrochloride |
| 23 | N-ethyl-4-[(2-isopropylphenyl)amino]-8-methoxy-quinoline-3-carboxamide hydrochloride |
| 24 | N-2-propenyl-8-methyl-4-[(2-propylphenyl)amino]quinoline-3-carboxamide |
| 25 | N-methyl-4-[(2-ethylphenyl)amino]-8-methoxyquinoline-3-carboxamide hydrochloride |
| 26 | N-[(2-methyl-2-propenyl)-8-ethyl-4-[(2-ethylphenyl)amino]quinoline-3-carboxamide |
| 27 | N-2-propenyl-8-chloro-4-[(2-isopropylphenyl)amino]quinoline-3-carboxamide hydrochloride |
| 28 | N-(2,2,2-trifluoroethyl)-8-methoxy-4-[(2-ethylphenyl)amino]quinoline-3-carboxamide hydrochloride |
| 29 | 4-[(2-methylphenyl)amino]quinoline-3-carboxylate hydrochloride (Control compound set forth in Japanese Unexamined Patent Application No. 147222/1990) |
| 30 | N-2-propenyl-8-chloro-4-[(2-n-propylphenyl)amino]quinoline-3-carboxamide hydrochloride |
| 31 | N-cyclopropylmethyl-8-methoxy-4-[(2-ethylphenyl)amino]quinoline-3-carboxamide |

TABLE 3

| Test Compound | $ED_{50}$ (mg/kg) |
|---|---|
| 1 | 6.72 |
| 2 | 0.996 |
| 3 | 1.7 |
| 4 | 7.1 |
| 5 | 2.8 |
| 6 | 1.4 |
| 7 | 6.8 |
| 8 | 3.5 |
| 9 | 4.2 |
| 10 | 1.6 |
| 11 | 2.09 |
| 12 | 6.7 |
| 13 | 6.7 |
| 14 | 8.7 |
| 15 | 7.74 |
| 16 | 5.7 |
| 17 | 2.4 |
| 18 | 2.2 |
| 19 | 4.4 |
| 20 | 3.2 |
| 21 | 6.9 |
| 22 | 5.6 |
| 23 | 7.6 |
| 24 | 1.9 |
| 25 | 5.3 |
| 26 | 3.0 |
| 27 | 4.0 |
| 28 | 4.9 |
| 30 | 1.4 |
| 31 | 4.3 |

(b) Aspirin Ulcer

Testing Method

In tests, there were used Wistar-type rats each having a weight of 160 to 180 g after 24-hour-fast. 200 Mg/kg of aspirin as suspended in 0.5%-carboxymethyl cellulose was orally administered to each of the rats. Five hours after administeration of aspirin, each rat was clubed to death and the stomach thereof was removed. Ten ml of a 1%-formalin solution was injected into the stomach, which was immersed in a 1%-formalin solution for 30 minutes. Thus, the stomach was fixed at the inner and outer layers thereof. Each stomach was cut out along the large curvature. The length of each ulcer was measured with a stereomicroscope (10 ×) and the total length was calculated as an ulcer coefficient.

Each test compound was orally administered in each of dosages of 0.3, 1, 3 and 10 mg/kg 30 minutes before administration of aspirin. According to a probit method, $ED_{50}$ was calculated from the inhibition percentage of each test compound with respect to the control compound.

The results are shown in Table 4.

TABLE 4

| Test Compound | $ED_{50}$ (mg/kg) |
|---|---|
| 2 | 0.48 |
| 3 | 0.42 |
| 5 | 4.2 |
| 6 | 2.6 |
| 7 | 4.0 |
| 10 | 2.7 |
| 11 | 2.7 |
| 18 | 3.3 |
| 22 | 4.3 |
| 29 | 9.1 |

(c) $H^+ + K^+$ ATPase Inhibitory Action $H^+ + K^+$ ATPase (adenosinetriphosphatase)(protein: 10 μg) prepared from the stomach of a pig was added to a pipes-Tris [2-amino-2-(hydroxymethyl)-1,3-propandiol] buffer (pipes-Tris buffer)(pH 8.1) containing 2 mM piperazine N,N′-bis(2-ethane sulfonic acid). The resultant reaction solution was allowed to stand at a room temperature. Each of the test compounds was dissolved in dimethyl formamide, which was added to the $H^+ + K^+$ ATPase buffer such that the final concentration was 1%. The resultant reaction solution was reacted at a room temperature for 30 minutes. In the same manner, another reaction solution was prepared. Respectively added to the reaction solutions were 1 ml of a 75 mM pipes-TRIS buffer (pH 7.4) (containing 4 mM $MgCl_2$, 4 mM $Na_2$ATP and 20 mM KCl) and 1 ml of a 75 mM pipes-Tris buffer (pH7.4) (containing 4 mM $MgCl_2$ and 4 mM $Na_2$ATP). Thus, two kinds of samples were prepared and reacted at 37° C. for 30 minutes. Added to each of the samples was 0.3 ml of 40% trichloroacetic acid, thus completing the reaction. After the samples were subjected to centrifugal separation (3,000 rpm) for 10 minutes. The supernatant liquids were taken to produce inorganic phosphoric acids, of which amounts were measured according to a Fiske and Subbarow method [J. Biol. Chem. vol. 86,375 (1925)]. The amount of the inorganic phosphoric acid obtained from the pipes-Tris buffer containing no 20 mM KCl was deducted from the amount of the inorganic phosphoric acid obtained from the pipes-Tris buffer containing 20 mM KCl. The difference expressed in terms of unit protein per unit time was defined as an enzyme active value. The inhibition value (%) of each dosage was obtained from the control value and the enzyme active value at each dosage. Based on the inhibition value thus obtained, $IC_{50}$ (the dosage of each test compound which achieves inhibition of 50%) was obtained.

The results are shown in Table 5.

TABLE 5

| Test Compound | $IC_{50}$ (M) |
|---|---|
| 2 | $2.2 \times 10^{-6}$ |
| 3 | $4.9 \times 10^{-6}$ |
| 5 | $1.6 \times 10^{-6}$ |

TABLE 5-continued

| Pharmaceutical Example 1 | |
|---|---|
| N-2-Propenyl-4-[(2-ethylphenyl)amino]-8-methoxyquinoline-3-carboxamide hydrochloride | 150 g |
| AVICEL (manufactured by Asahi Kasei Co., Ltd.) | 40 g |
| Corn starch | 30 g |
| Magnesium stearate | 2 g |
| Hydroxypropyl methyl cellulose | 10 g |
| Polyethylene glycol-6000 | 3 g |
| Castor oil | 40 g |
| Methanol | 40 g |

The compound of the present invention, AVICEL, corn starch and magnesium stearate were mixed, polished and then tableted by means of a R10mm punch (for sugar-coated tablets). The tablets thus obtained were coacted with a film comprising hydroxypropyl methyl cellulose, polyethylene glycol-6000, castor oil and methanol to prepare film-coated tablets.

| Pharmaceutical Example 2 | |
|---|---|
| N-2-propenyl-4-[(2-ethylphenyl)amino-8-methoxyquinoline-3-carboxamide hydrochloride | 150 g |
| Citric acid | 1.0 g |
| Lactose | 33.5 g |
| Dipotassium phosphate | 70.0 g |
| Pruronic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | suitable amount |

The compound of the present invention, citric acid, lactose, dipotassium phosphate, Pruronic F-68 and sodium lauryl sulfate were mixed.

After put through a No. 60-screen, the resultant mixture was wet-granulated with an alcoholic solution containing polyvinyl pyrrolidone, carbowax 1500 and carbowax 6000. As necessary, alcohol was added to the resulting powder, causing the powder to be pasted. Corn starch was added to the pasted body, which was ten continuously mixed until uniform particles were obtained. After put through a No. 10-screen, the particles were put in a tray and then dried in an oven at 100° C. for 12 to 14 hours. After put through a No. 16-screen, the dried particles were added to and mixed with dry sodium lauryl sulfate and dry magnesium stearate. The resultant mixture was compressed into a desired shape with a tablet compressing machine.

Treated with varnish were the centers of the tablets thus prepared, to which talc was sprayed to prevent the absorption of moisture. The tablets were coated at the circumferences of the center portions thereof with preliminary layers. The tablets were coated with varnish a number of times sufficient to make them to be applied for internal use. To make the tablets perfectly round and smooth, the tablets were further coated with preliminary layers and smoothing layers. The tablets were coated with coloring agents until a desired color hue was obtained. After dried, the coated tablets were polished to prepare tablets presenting a uniform luster.

What is claimed is:

1. A quinoline derivative or salt thereof represented by the following general formula:

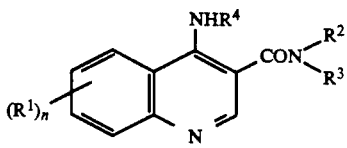

wherein $R^1$ is a lower alkoxy group, a halogen atom, a lower alkyl group, a lower alkylthio group, a lower alkanoyloxy-lower alkyl group, a halogen-substituted lower alkyl group or a hydroxy-group-substituted lower alkyl group; $R^2$ and $R^3$ may be the same as or different from each other and each is a hydrogen atom, a lower alkyl group, a halogen-substituted lower alkyl group, a cycloalkyl group having 3 to 8 carbon atoms, a cycloalkyl lower alkyl group, a lower alkenyloxy group, a lower alkenyl group, a lower alkoxy-lower alkyl group, a phenyl lower alkyl group, a lower alkynyl group, a phenyl group having a lower alkyl group as a substituent group, or a hydroxy-group-substituted lower alkyl group; $R^4$ is a phenyl, tetrahydronaphthyl or naphthyl group which may have, as a substituent group on the phenyl ring, one or two groups selected from the group consisting of a lower alkyl group, a halogen atom, a lower alkoxy group, a lower alkylthio group, a lower alkanoyl group, a phenyl group, a cyano group, a lower alkyl sulfinyl group, a lower alkoxycarbonyl group, a lower alkenylthio group, a phenyl lower alkylthio group, a benzoyl group, a hydroxy-group-substituted lower alkyl group, a lower alkanoyloxy-lower alkyl group, a lower alkanoyloxy group and a hydroxy group; and n is 0, 1 or 2.

2. A quinoline derivative and salt thereof according to claim 1, wherein $R^2$ and $R^3$ are same as or different from each other, and each is a hydrogen atom, a lower alkyl group or a lower alkenyl group.

3. A quinoline derivative and salt thereof according to claim 1, wherein $R^2$ and $R^3$ are the same as or different from each other and each is a halogen-substituted lower alkyl group, a cycloalkyl group having 3 to 8 carbon atoms, a cycloalkyl lower alkyl group, a lower alkenyloxy group, a lower alkoxy-lower alkyl group, a phenyl lower alkyl group, a lower alkynyl group, a phenyl group having a lower alkyl group as a substituent group or a hydroxy-group-substituted lower alkyl group.

4. A quinoline derivative and salt thereof according to claim 1, wherein $R^2$ and $R^3$ are same as or different from each other and each is a hydrogen atom, a lower alkyl group, or a lower alkynyl group, $R^1$ is a lower alkoxy group or a lower alkyl group and $R^4$ is a phenyl group having one or two lower alkyl groups as substituent groups on the phenyl ring.

5. A quinoline derivative and salt thereof according to claim 2, wherein $R^1$ is a lower alkoxy group or a lower alkyl group.

6. A quinoline derivative and salt thereof according to claim 2, wherein $R^1$ is a halogen atom, a lower alkylthio group, a lower alkanoyloxy-lower alkyl group, a halogen-substituted lower alkyl group or a hydroxy-group-substituted lower alkyl group.

7. A quinoline derivative and salt thereof according to claim 3, wherein $R^1$ is a lower alkoxy group or a lower alkyl group.

8. A quinoline derivative and salt thereof according to claim 3, wherein $R^1$ is a halogen atom, a lower alkylthio group, a lower alkanoyloxy-lower alkyl group, a halogen-substituted lower alkyl group or a hydroxy-group-substituted lower alkyl group.

9. A quinoline derivative and salt thereof according to any of claims 5, 6, 7 and 8, wherein $R^4$ is a phenyl group or a phenyl group having, as a substituent group on the phenyl ring, one or two groups selected from the group consisting of a lower alkyl group, a halogen atom, a lower alkoxy group, a lower alkylthio group, a lower alkanoyl group, a phenyl group, a cyano group, a lower alkyl sulfinyl group, a lower alkoxycarbonyl group, a lower alkenylthio group, a phenyl lower alkylthio group, a benzoyl group, a hydroxy-group-substituted lower alkyl group, a lower alkanoyloxy-lower alkyl group, a lower alkanoyloxy group and a hydroxy group.

10. A quinoline derivative and salt thereof according to any of claims 5, 6, 7 and 8, wherein $R^4$ is a tetrahydronapthyl or naphthyl group.

11. N-2-propenyl-8-methoxy-4-[(2-ethylphenyl)amino] quinoline-3-carboxamide.

12. N-2-propenyl-8-methoxy-4-[(2-isopropylphenyl)amino] quinoline-3-carboxamide.

13. N-2-propenyl-8-methoxy-4-[(2-n-propylphenyl)amino] quinoline-3-carboxamide.

14. N-2-propenyl-8-ethyl-4-[(2-methylphenyl)amino] quinoline-3-carboxamide.

15. N-2-propenyl-8-methyl-4-[(2-n-propylphenyl)amino] quinoline-3-carboxamide.

16. N-ethyl-8-ethyl-4-[(2-methylphenyl)amino] quinoline-3-carboxamide.

17. An antiulcer agent containing, as effective components, an effective amount of the quinoline derivative and salt thereof set forth in claim 1 in combination with a pharmaceutical acceptable carrier.

* * * * *